(12) United States Patent
Honjo et al.

(10) Patent No.: US 9,783,609 B2
(45) Date of Patent: *Oct. 10, 2017

(54) SUBSTANCE SPECIFIC TO HUMAN PD-1

(71) Applicants: ONO PHARMACEUTICAL CO., LTD., Osaka (JP); Tasuku Honjo, Kyoto-shi, Kyoto (JP)

(72) Inventors: Tasuku Honjo, Kyoto (JP); Shiro Shibayama, Osaka (JP); Kazuhiko Takeda, Osaka (JP); Masayoshi Matsuo, Osaka (JP); Takao Yoshida, Osaka (JP); Masakazu Miyamoto, Osaka (JP)

(73) Assignees: ONO PHARMACEUTICAL CO., LTD., Osaka (JP); Tasuku Honjo, Kyoto (JP)

( * ) Notice: Subject to any disclaimer, the term of this patent is extended or adjusted under 35 U.S.C. 154(b) by 326 days.

This patent is subject to a terminal disclaimer.

(21) Appl. No.: 14/584,664

(22) Filed: Dec. 29, 2014

(65) Prior Publication Data
US 2015/0118234 A1 Apr. 30, 2015

Related U.S. Application Data

(60) Continuation of application No. 13/548,807, filed on Jul. 13, 2012, now Pat. No. 8,951,518, which is a division of application No. 13/169,278, filed on Jun. 27, 2011, now Pat. No. 8,246,955, which is a division of application No. 12/469,188, filed on May 20, 2009, now Pat. No. 7,998,479, which is a continuation of application No. 10/543,323, filed as application No. PCT/JP2004/000549 on Jan. 22, 2004, now Pat. No. 7,563,869.

(30) Foreign Application Priority Data

Jan. 23, 2003 (JP) ................................ 2003-14793

(51) Int. Cl.
C07K 16/28 (2006.01)
A61K 39/395 (2006.01)
A61K 39/00 (2006.01)

(52) U.S. Cl.
CPC ...... *C07K 16/2818* (2013.01); *A61K 39/3955* (2013.01); *C07K 16/2803* (2013.01); *C07K 16/2809* (2013.01); *A61K 2039/505* (2013.01); *C07K 2317/31* (2013.01); *C07K 2317/56* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 5,932,449 A | 8/1999 | Emanuel et al. | |
| 6,111,079 A | 8/2000 | Wylie et al. | |
| 6,808,710 B1 | 10/2004 | Wood et al. | |
| 7,029,674 B2 | 4/2006 | Carreno et al. | |
| 7,998,479 B2 | 8/2011 | Honjo et al. | |
| 8,246,955 B2 * | 8/2012 | Honjo ................ | C07K 16/2803 424/136.1 |
| 8,951,518 B2 * | 2/2015 | Honjo ................ | C07K 16/2803 424/136.1 |
| 2005/0004352 A1 | 1/2005 | Kontermann et al. | |

FOREIGN PATENT DOCUMENTS

| | | |
|---|---|---|
| EP | 1334659 A1 | 8/2003 |
| EP | 1445264 A1 | 8/2004 |
| JP | 2000201678 A | 7/2000 |
| WO | 01/14557 A1 | 3/2001 |
| WO | 01/64249 A1 | 9/2001 |
| WO | 02/078731 A1 | 10/2002 |

OTHER PUBLICATIONS

Salama et al. (Journal of Experimental Medicine, 2003, 198: 71-78).*
Declaration by Shiro Shibayama, filed on Apr. 1, 2011 in U.S. Appl. No. 12/469,188; 2 pages.*
Supplemental European Search Report issued Apr. 11, 2006 in EP 04704324.5.
Gordon J. Freeman et al., "Engagement of the PD-1 Immunoinhibitory Receptor by a Novel B7 Family Member Leads to Negative Regulation of Lymphocyte Activation", J. Exp. Med., 2000, 192(7): 1027-1034.
Engin Ozkaynak et al., "Programmed Death-1 Targeting Can Promote Allograft Survival", The Journal of Immunology, 2002, 169:6546-6553.
Laura L. Carter et al., "PD-1: PD-L inhibitory pathway affects both CD4 and CD8 T cells and is overcome by IL-2", Eur. J. Immunol., 2002, 32: 634-643.
Margitta ALT et al., "Novel tetravalent and bispecific IgG-like antibody molecules combining single-chain diabodies with the immunoglobulin ADDSYMB1 Fc or CH3 region", FEBS Letters, 1999, 454: 90-94.
Peter J. Hudson et al., "High avidity scFv multimers; diabodies and triabodies", Journal of Immunological Methods, 1999, 231: 177-189.
Sequence Alignment, Sequence 18 of U.S. Pat. No. 6,111,079, 2008.
Tina Volkel et al., "Optimized linker sequences for the expression of monomeric and dimeric bispecific single-chain diabodies", Protein Engineering, 2001, 14(10): 815-823.
Ziwei Huang, "Structural chemistry and therapeutic intervention of protein-protein interactions in immune response, human immunodeficiency virus entry, and apoptosis", Pharmacology & Therapeutics, 2000, 86:201-215.

(Continued)

*Primary Examiner* — Ilia Ouspenski
(74) *Attorney, Agent, or Firm* — Sughrue Mion, PLLC

(57) ABSTRACT

The present invention relates to a substance specific to human PD-1 comprising a part that recognizes human PD-1, a part that recognizes a membrane protein in cell membrane of human PD-1-expressing cells, and linkers. Since the substance specific to human PD-1 selectively can recognize human PD-1 and a membrane protein on cell membrane of human PD-1-expressing cells and can transmit inhibitory signal of human PD-1, it is useful for therapy and/or prevention of diseases caused by immunopathy.

8 Claims, 2 Drawing Sheets

(56) References Cited

OTHER PUBLICATIONS

Teresa K. Attwood, "The Babel of Bioinformatics", Science, 2000, 290: 471-473.
Jeffrey Skolnick et al., "From genes to protein structure and function: novel applications of computational approaches in the genomic era", Tibtech, 2000, 18(1): 34-39.
Bruce R. Blazar et al., "Infusion of Anti-B7.1 (CD80) and Anti-B7.2 (CD86) Monoclonal Antibodies Inhibits Murine Graft-Versus-Host Disease Lethality in Part Via Direct Effects on CD4+ and CD8+ T Cells", The Journal of Immunology, 1996, 157: 3250-3259.
Zuberek K, et al., "The Role of in Vivo PD-1/PD-L1 Interactions in Syngeneic and Allogeneic Antitumor Responses in Murine Tumor Models", Blood, American Society of Hematology, US, vol. 98, No. 11, Part 02, Dec. 11, 2001 (Dec. 11, 2001), p. 42B, ABSTRACT3772, XP008068416, ISSN : 0006-4971.
Office Action, dated Jan. 7, 2013, issued by the European Patent Office in counterpart European Applicant No. 04 704 324.5.
Office Action, dated Jan. 7, 2013, issued by the European Patent Office in counterpart European Divisional Application No. 10 176 748.1.
Bennett, Fran et al. "Program Death-1 Engagement Upon TCR Activation has Distinct Effects on Costimulation and Cytokine-driven Proliferation: Attenuation of ICOS, IL-4, and IL-21, but not CD28, IL-7, and IL-15 Responses." The Journal of Immunology 170.2 Jan. 1, 2003 (Jan. 1, 2003): 711-718. XP055048008, ISSN:0022-1767.
Holliger, Philipp, et al., ""Diabodies": Small bivalent and bispecific antibody fragments", Proc. Natl. Acad. Sci. USA: Biophysics, Jul. 1993, pp. 6444-6448.
Perisic, Olga, et al., "Crystal structure of a diabody, a bivalent antibody fragment," Current Biology Ltd., ISSN 0969-2126, 1994, vol. 2, No. 12, pp. 1217-1226.
Takemura, Shin-ichi, et al., "Construction of a diabody (small recombinant bispecific antibody) using a refolding system", Protein Engineering, 2000, vol. 13, No. 8, pp. 583-588.
Godeau, Francois, et al., "Purification and Ligand Binding of a Soluble Class I Major Histocompatibility Complex Molecule Consisting of the First Three Domains of H-2Kd Fused to Beta2-Microglobulin Expressed in the Baculovirus-Insect Cell System", The Journal of Biological Chemistry, The American Society for Biochemistry and Molecular Biology, Inc., 1992, vol. 267, No. 34, Issue Dec. 5, 1992, pp. 24223-24229.
Office Action dated May 23, 2014 issued by the Japanese Patent Office in counterpart Japanese Patent Application No. 2012-256828.
Aly et al., Am. J. Therapeutics (2005) 12:481-490.
Mayo Foundation, 2012, accessed at mayoclinic.com/health/type-1-diabetes/DS00329 on Sep. 13, 2012; 20 pages.
Office Action, dated Aug. 24, 2015, issued by the Japanese Patent Office in counterpart Japanese Patent Application No. 2012-256828.
Ziwei Huang, "Structural chemistry and therapeutic intervention of protein-protein interactions in immune response, human immunodeficiency virus entry, and apoptosis", Pharmacology & Therapeutics, 2000, 86: 201-215.
Zuberek K, et al., "The Role of in Vivo PD-1/PD-L1 Interactions in Syngeneic and Allogeneic Antitumor Responses in Murine Tumor Models", Blood, American Society of Hematology, US, vol. 98, No. 11, Part 02, Dec. 11, 2001 (Dec. 11, 2001), p. 42B, Abstract 3772, XP008068416, ISSN : 0006-4971.
Communication from the European Patent Office dated Sep. 19, 2011, in counterpart EP Application No. 04704324.5 (in the name of Ono Pharmaceutical Co., Ltd.).
Declaration by Shiro Shibayama, filed in U.S. Appl. No. 12/469,188 on Apr. 1, 2011.
R.L. Rabin et al., "The nexus between atopic disease and autoimmunity: a review of the epidemiological and mechanistic literature", Clinical & Experimental Immunology, 2008, 153: 19-30.
Alan D. Salama et al., "Critical Role of the Programmed Death-1 (PD-1) Pathway in Regulation of Experimental Autoimmune Encephalomyelitis", Journal of Experimental Medicine, 2003, 198(1): 71-78.
Communication dated Nov. 17, 2016, issued by the Japanese Patent Office in counterpart Japanese application No. 2015-239678.

* cited by examiner

SUBSTANCE SPECIFIC TO HUMAN PD-1

CROSS-REFERENCE TO RELATED APPLICATIONS

This is a continuation application of application Ser. No. 13/548,807 filed Jul. 13, 2012, which is a divisional application of application Ser. No. 13/169,278 filed Jun. 27, 2011 (now U.S. Pat. No. 8,246,955), which is a divisional application of application Ser. No. 12/469,188 filed May 20, 2009 (now U.S. Pat. No. 7,998,478), which is a continuation application of application Ser. No. 10/543,323 filed Jul. 25, 2005 (now U.S. Pat. No. 7,563,869), which is a National Stage Application filed under §371 of PCT Application No. PCT/2004/000549 filed Jan. 22, 2004. The entire disclosures of the prior applications are hereby incorporated by reference.

FIELD OF THE INVENTION

The present invention relates to antibodies specific to human PD-1, bispecific antibodies comprising antibodies against human T cell receptor complex or human B cell receptor complex, polynucleotides encoding them, and the usage of the bispecific antibodies.

BACKGROUND OF THE INVENTION

The immune system acquired the mechanism that can respond to various foreign antigens. The mechanism takes the diversity of an antigen receptor by recombination of V, (D) and J fragment in T cells and B cells. Although this mechanism brought about a result that produces autoreactive lymphocytes, these autoreactive lymphocytes are removed by the negative selection in thymus or bone marrow, and are further controlled by the self-tolerance mechanism of clonal deletion or anergy in periphery.

Although it is thought that an autoimmune disease is developed by the breakdown of self-tolerance, the researches using various disease murine model have been conducted to elucidate the mechanism of pathogenesis. However, the etiology of an autoimmune disease and the molecular mechanism of self-tolerance remain unclear. In such a situation, existence of the mouse which shows the symptoms of an autoimmune disease caused by a single gene deficient is very important for study the etiology of an autoimmune disease from a molecular biological viewpoint. CTLA4−/− mouse which causes lethal systemic lymphocytes infiltration (Waterhouse P., et al., *Science*, 270:985-988, 1995, Tivol E. A., et al., *Immunity*, 3:541-547, 1995), SHP-1 deficient mothaten mice (Shulltz L. D., et al., *Cell*, 73:1445-1454, 1993), lyn−/−mouse which shows the symptoms of glomerular nephritis (Hibbs M. L., et al., *Cell*, 83:301-311, 1995), and FCRIIB−/−mouse (Bolland S. & Ravetch J. V., *Immunity*, 13:277-285, 2000) are the representation, and the relations of these molecules and self-tolerance has been studied.

The PD-1 gene, which belongs to the immunoglobulin super family, encodes a 55 kDa type I transmenbrane protein. Both mouse PD-1 and human PD-1 consist of 288 amino acids, and have signal peptide at N terminal (20 amino acid) and hydrophobic region in the middle part, which is a transmembrane region (*The EMBO J.*, 11(11): 3887-3895, 1992); Japanese patent Publication No. 5-336973; EMBL/GenBank/DDJB Acc. No. X67914, *Genomics*, 23:704, 1994; Japanese patent Publication No. 7-291996 (U.S. Pat. No. 5,629,204).

In thymus, PD-1 is expressed at the transition phase between CD4−/CD8− to CD4+/CD8+ stage on thymocytes (Nishimura H., et al., *Int. Immunol.*, 8:773-780 (1996), Nishimura H., et al., *J. Exp. Med.*, 191:891-898 (2000)). In periphery, PD-1 is expressed on T cells and B cells activated through the antigen receptor (Agata Y., et al., *Int. Immunol.*, 8:765-772 (1996)), and on activated myeloid lineage cells such as macrophages.

PD-1 has ITIM (Immunoreceptor tyrosine-based inhibitory motif) in its intracellular region. Therefore, PD-1 is a negative regulator in immune responses. Since PD-1 deficient mice developed a lupus-like glomerular nephritis and arthritis (C57BL/6 genetic background) (Nishimura H., et al., *Int. Imuunol.*, 10:1563-1572, 1998, Nishimura H., et al., *Immunity*, 11:141-151, 1999) and dilated cardiomyopathy-like disease (BALB/c genetic background) (Nishimura H., et al., *Science*, 291:319-322 (2001)), it became clear that PD-1 serves as a regulator for the development of autoimmune disease, especially for the maintenance of self tolerance. Further it has been reported that graft rejection is regulated by inhibition of PD-1 signal (*Journal of Immunology*, 169, 11:6543-6553 (2001)).

DISCLOSURE OF THE INVENTION

It is thought that PD-1 is a regulator of various autoimmune diseases, and that it is one of causative genes of autoimmune diseases. Control of the PD-1 function can bring about the medical treatment and diagnosis of suppression or enhancement of the immune function, infection, transplant rejection, and neoplasm etc. As a result of keen examination, the present inventors reached the present invention concerning the substances that controls the function of PD-1.

Stimuli on lymphocytes which control immunity are transmitted mainly through T cell receptor (TCR) in case of T cells, and B cell receptor (BCR) in case of B cells, and then intracellular phosphorylation plays an important role in the molecular mechanism.

Since it has been elucidated that PD-1 negatively regulates various immunocompetent cells such as lymphocytes and myeloid cells etc. and PD-1 has ITIM (Immunoreceptor tyrosine-based inhibitory motif) in its intracellular region, the present inventors considered that the recruit of de-phosphorylation enzymes (phosphatases) could be involved in the molecular mechanism in the inhibitory signal transduction mediated by PD-1. Therefore, it was hypothesized that making PD-1 colocalize with TCR or BCR can display the PD-1 function.

The present inventors confirmed that the inhibitory signal of PD-1 was transmitted with the substance which physically cross-links PD-1 to TCR or BCR. First, the present inventors confirmed that the above idea was right using anti-PD-1 antibodies and anti-CD3 antibodies. CD3 is a membrane protein expressed on T cells and is one component of TCR complexes. The divalent antibodies were constructed by bridging anti-PD-1 antibodies and anti-CD3 antibodies. The present invention was completed by isolating each cDNA encoding anti-human PD-1 antibody and anti-human TCR antibody and producing bispecific antibody produced by constructing expression vectors that can express fusions proteins comprising each antigen-recognition site of both antibodies.

The present invention relates to the followings:
(1) A substance specific to human PD-1 comprising a part that recognizes human PD-1, a part that recognizes a (1) ...membrane protein on cell membrane of human PD-1-expressing cells, and a linker.
(2) The substance specific to human PD-1 according to (1), wherein the part that recognizes human PD-1 is an antibody against human PD-1 or a partial fragment thereof.
(3) The substance specific to human PD-1 according to (1), wherein the part that recognizes a membrane protein on cell membrane of human PD-1-expressing cells is an antibody against the membrane protein or a partial fragment thereof.
(4) The substance specific to human PD-1 according to (1), comprising an antibody against human PD-1 or a partial fragment thereof, an antibody against the membrane protein on cell membrane of human PD-1-expressing cells or a partial fragment thereof, and a linker.
(5) The substance specific to human PD-1 according to any one of (1), (3) and (4), wherein the membrane protein is human T cell receptor complex or human B cell receptor complex.
(6) The substance specific to human PD-1 according to (1) or (4), wherein the linker is a peptide.
(7) A bispecific antibody comprising an antibody against human PD-1 or a partial fragment thereof, an antibody against human T cell receptor complex or a partial fragment thereof, and a linker.
(8) A bispecific antibody comprising an antibody against human PD-1 or a partial fragment thereof, an antibody against human B cell receptor complex or a partial fragment thereof, and a linker.
(9) The bispecific antibody according to (7) or (8), wherein the linker is a peptide.
(10) A substantially pure polypeptide comprising the amino acid sequence represented by SEQ ID NO:2, a homolog thereof, a fragment thereof or a homolog of the fragment, or a polypeptide comprising the amino acid sequence to which 1-10 amino acid(s) of the polypeptide is/are deleted, substituted, and/or added, wherein the polypeptide composes an antibody against human PD-1.
(11) A substantially pure polypeptide comprising the amino acid sequence represented by SEQ ID NO:4, a homolog thereof, a fragment thereof or a homolog of the fragment, or a polypeptide comprising the amino acid sequence to which 1-10 amino acid(s) of the polypeptide is/are deleted, substituted, and/or added, wherein the polypeptide composes an antibody against human PD-1.
(12) A polypeptide complex comprising the polypeptides according to (10) and (11).
(13) A substantially pure polypeptide comprising the amino acid sequence represented by SEQ ID NO:11, a homolog thereof, a fragment thereof or a homolog of the fragment, or a polypeptide comprising the amino acid sequence to which 1-10 amino acid(s) of the polypeptide is/are deleted, substituted, and/or added.
(14) A substantially pure polypeptide comprising the amino acid sequence represented by SEQ ID NO:11, a homolog thereof, a fragment thereof or a homolog of the fragment, or a polypeptide comprising the amino acid sequence to which 1-10 amino acid(s) of the polypeptide is/are deleted, substituted, and/or added, which is the bispecific antibody according to any one of (7) to (9).
(15) A polynucleotide encoding the polypeptide according to any one of (10), (11), (13) and (14), a homolog thereof or a complementary polynucleotide thereof, or a fragment thereof or a homolog of the fragment.
(16) A polynucleotide comprising the nucleotide sequence represented by SEQ ID NO:1, SEQ ID NO:3, or SEQ ID NO:9, a homolog thereof or a complementary polynucleotide thereof, or a fragment thereof or a homolog of the fragment.
(17) A duplication or expression vector comprising the polynucleotide according to (15) or (16).
(18) A host cell transformed by the duplication or expression vector according to (17).
(19) A manufacturing method of the substance according to any one of (1) to (6), comprising culturing the host cell according to (18) under conditions to express the substance.
(20) A manufacturing method of the bispecific antibody according to any one of (7) to (9), comprising culturing the host cell according to (18) under conditions to express the bispecific antibody.
(21) A manufacturing method of the polypeptide according to any one of (10) to (14), comprising culturing the host cell according to (18) under conditions to express the polypeptide.
(22) A therapeutic and/or preventive pharmaceutical composition for human PD-1 related-diseases, comprising an effective amount of the substance according to any one of (1) to (6), the bispecific antibody according to any one of (7) to (9), the polypeptide complex according to (12), or the polypeptide according to (13) or (14).
(23) The therapeutic and/or preventive pharmaceutical composition according to (22), wherein the human PD-1 related-diseases are diseases selected from neurodegenerative disease, autoimmune disease, collagenosis, organ transplantation rejection, tumour, and infectious disease.
(24) The therapeutic and/or preventive pharmaceutical composition according to (22), wherein the neurodegenerative diseases are diseases selected from geriopsychosis, Alzheimer disease, Down syndrome, Parkinson's disease, Creutzfeldt-jakob disease, diabetic neuropathy, Parkinson syndrome, Huntington's disease, Machado-Joseph disease, amyotrophic lateral sclerosis, diabetic neuropathy, and Creutzfeldt Creutzfeldt-Jakob disease.
(25) The therapeutic and/or preventive pharmaceutical composition according to (22), wherein the autoimmune diseases are diseases selected from glomerular nephritis, arthritis, dilated cardiomyopathy-like disease, ulceous colitis, Sjogren syndrome, Crohn disease, systemic erythematodes, chronic rheumatoid arthritis, multiple sclerosis, psoriasis, allergic contact dermatitis, polymyosiis, pachyderma, periarteritis nodosa, rheumatic fever, vitiligo vulgaris, insulin dependent diabetes mellitus, Behcet disease, Hashimoto disease, Addison disease, dermatomyositis, myasthenia gravis, Reiter syndrome, Graves' disease, anaemia perniciosa, Goodpasture syndrome, sterility disease, chronic active hepatitis, pemphigus, autoimmune thrombopenic purpura, and autoimmune hemolytic anemia.

The part that recognizes human PD-1 in the present invention has only to be a substance that recognizes human PD-1, for example, anti-human PD-1 antibody or a fragment thereof, human PD-1 itself or a fragment thereof, a ligand for human PD-1 or a fragment thereof (Freeman, G J, et al., *Journal of Experimental Medicine*, 19, 7; 1027-1034 (2000)), human PD-L2, and human PD-H3 etc.), and a low molecular weight organic compounds etc.

The antibody for human PD-1 or a fragment thereof may be either of complete polyclonal or monoclonal antibody, humanized antibody, complete human antibody, and short antibody thereof (for example, F(ab')$_2$, Fab', Fab, Fv) etc. which contains anti-human PD-1 antibody or a fragment thereof.

Concretely, they are monoclonal anti-human PD-1 antibodies produced by hybridomas (International Trust Number FERM P-19162) that had been deposited to National Institute of Advanced Industrial Science and Technology, International Patent Organism Depositary in Central 6, 1-1-1 Higashi, Tsukuba, Ibaraki, Japan at Dec. 19, 2002, and had been transferred to International Deposit at Jun. 5, 2003 (International Trust Number FERM BP-8392), which was named J110. Though F(ab')$_2$, Fab', Fab, and Fv antibody fragments of these antibodies etc. are preferable, they don't limit to them.

F(ab')$_2$, Fab', Fab, and Fv antibody fragments can be obtained by processing complete antibodies with protease enzyme, and optionally reducing it. They can be produced as antibodies, fragments of thereof, or fusion proteins with another proteins and the fragments, by using the expression vector made by gene rearrangement using the cDNA separated from antibody-producing hybridoma.

The membrane protein on cell membrane of human PD-1-expressing cells means the membrane protein that expresses on cell membrane of the same cell as human PD-1-expressing cells, and includes each the membrane protein of human PD-1-expressing human first stage culture cells or human cell lines. For example, T cell receptor complex or B cell receptor complex is preferable.

The part that recognizes the membrane protein on cell membrane of human PD-1-expressing cells may be a substance that recognizes the membrane protein that expresses on cell membrane of the same cell as human PD-1-expressing cells, and includes, for example, antibodies against the membrane protein and fragments thereof, the membrane protein itself and fragments thereof, ligands for the membrane protein and fragments thereof, and low molecular weight organic compounds that bind to the membrane protein etc.

The antibodies or partial fragments thereof to the membrane protein on cell membrane of human PD-1-expressing cells are antibodies or partial fragments thereof to the membrane protein that expresses on cell membrane of the same cell as human PD-1-expressing cells, and may be either of complete polyclonal or monoclonal antibodies, humanized antibodies, complete human antibodies, and short antibodies thereof (for example, F(ab')$_2$, Fab', Fab, Fv) etc.

T cell receptor complex is at least a complex comprising T cell receptor consisting of α subunit and β subunit and CD3 consisting of γ subunit, δ subunit, ε subunit, and ζ subunit.

B cell receptor complex is at least a complex comprising membrane-bound immunoglobulin, CD79α subunit, and CD79β subunit.

The antibodies or partial fragments thereof to T cell receptor complex may be either of antibodies or partial fragments thereof that recognize T cell receptor complex. They include antibodies or partial fragments thereof to each subunit of T cell receptor and CD3, which composes T cell receptor complex and may be either of complete polyclonal or monoclonal antibodies, humanized antibodies, complete human antibodies, and short antibodies thereof (for example, F(ab')$_2$, Fab', Fab, Fv) etc. For example, the monoclonal antibodies against CD3 can be produced by using hybridoma that has already been established. Anti-CD3 (α-CD3εmAb (PharMingen, Inc.)) can be bought.

The antibodies or partial fragments thereof to B cell receptor complex may be either of antibodies or partial fragments thereof that recognize B cell receptor complex. They include antibodies or partial fragments thereof to each subunit of membrane-bound immunoglobulin and CD79, which composes B cell receptor complex, and may be either of complete polyclonal or monoclonal antibodies, humanized antibodies, complete human antibodies, and short antibodies thereof (for example, F(ab')$_2$, Fab', Fab, Fv) etc. Concretely, commercial anti-BCR antibodies can be used and, for example, anti-IgG (H+L) polyclonal antibodies can be bought (Zymed Laboratories).

The substance comprising the part that recognizes human PD-1 and the part that recognizes the membrane protein on cell membrane of human PD-1-expressing cells means a substance that can simultaneously bind to an extracellular domain of human PD-1 and an extracellular domain of the membrane protein on cell membrane of the same cell. Concretely, they include bispecific antibodies comprising specific antibodies or fragments thereof to human PD-1 and specific antibodies or fragments thereof to the membrane protein on cell membrane of human PD-1-expressing cells.

The bispecific antibodies are unsymmetrical antibodies having two independent antigen-recognition sites with two different antigenic specificities. A well-known chemical method (Nisonoff, A., et al., *Archives of Biochemistry and Biophysics.*, 90; 460-462 (1961), Brennan, M., et al, *Science*, 299; 81-83 (1985)) is already well-known as a preparation method of the bispecific antibodies. The bispecific antibodies can be obtained by respectively hydrolyzing two kinds of antibodies by enzyme and cutting disulfide bonds of the H chains by reducing agents, and then mixing and reoxidizing the different kind of antibodies. Recently, the preparation method using cross linking agents such as glutaraldehyde and carbodiimide has been disclosed (JP02-01556).

Technologies that directly produce the bispecific antibodies by using gene recombination technologies have been known. For example, the producing of bispecific antibodies (called single chain diabody.) to carcinoembryonic antigen and *E. coli* beta-galactosidase has been reported in Alt, *FEBS Letter*, 454, 90 (1999). A heavy chain variable domain (VH) and other light chain variable domain (VL) of the fragment are connected with linkers to make them combine between two continuous domains on the same chain. A heavy chain variable domain (VH) and other light chain variable domain (VL) of the fragment are connected with linkers to make them combine between two continuous domains on the same chain. Therefore, VH and VL domain of the fragment are unavoidable to combine with complementary VL and VH domain of another fragment, as a result, two antigen binding sites are formed. Though 3-12 amino acid residues are preferable for the peptide linkers, the sequence is not limited (Hudson, P J., et al, *Journal of Immunology Medicine*, 231, 1-2; 177-189 (1999)).

As manufacturing of the bispecific antibodies using hybridomas, there is Reading, et al's method, that is, a method of producing hybrid hybridomas by further fusing two kinds of hybridomas that produce the monoclonal antibodies and then selecting hybrid hybridomas that produce target bispecific antibodies (U.S. Pat. No. 4,474,893).

The bispecific antibodies comprising specific antibodies or fragments thereof to human PD-1 and specific antibodies or fragments thereof to the membrane protein on cell membrane of human PD-1-expressing cells are antibodies that can simultaneously bind to the extracellular domain of human PD-1 and the extracellular domain of the membrane protein on cell membrane of the same cell.

The bispecific antibodies can be produced by the following method;
(1) animals are sensitized by human PD-1 or human membrane protein as an immunogen,
(2) splenic cells from the sensitized animals and myeloma cells from syngeneic animals are fused,
(3) cells that produce monoclonal antibodies against the sensitizing antigen (human PD-1 or human membrane protein) are screened from the obtained hybridomas,
(4) target antibodies-producing hybridomas are cloned,
(5) the cloned antibodies-producing hybridomas are proliferated,
(6) the produced antibodies are separated and refined,
(7) the bispecific antibodies are produced by cross-linking the obtained anti-human PD-1 antibodies and anti-human membrane protein antibodies with linkers, or
(8) they are further digested by pepsin and are separated, and refined to obtain $F(ab')_2$,
(9) each prepared $F(ab')_2$ is reduced and is separated and refined,
(10) the bispecific antibodies can be produced by cross-linking each prepared $Fab_{SH}$ by linkers.

The linkers are not limited and may be anything that can link the part that recognizes the membrane protein of PD-1-expressing cells to the part that recognizes human PD-1, keeping an appropriate range. More concretely, they include peptides and amides etc.

The commercial products, for example, phenylenedimaleimide (Aldrich) can be used as the linkers.

When both or one of substances that respectively recognize the membrane protein of PD-1-expressing cells and human PD-1 is/are low-molecular weight organic compound(s),
(11) using the antibodies produced by the above technique, the low-molecules that inhibit a bond between human membrane protein or human PD-1 and each antibody are found by measuring with a suitable detector,
(12) the antibody can be produced by cross-linking the low-molecules, the antibodies, or the Fab with linkers.

It concretely explains each process as follows.
(1) In sensitization, it is preferable that human PD-1 or human membrane protein is administrated to peritoneal cavity or foot pat of sensitized animals. And, the sensitized animals have only to be animals such as mouse and rat etc. that the monoclonal antibody can be obtained in general and are not limited. For example, it is enough that 10-200 μg of the antigen are administrated to mouse once.

A spleen of the sensitized animal that antibody titer has risen enough among the sensitized animals in previous (1) is removed. Suspension of the splenic cells is prepared according to the usual manner. Then, cell fusion of previous (2) is performed by adding polyethylene glycol (preferably PEG4000.) to the mixture with the obtained splenic cells and syngeneic myeloma cells at 37° C. Several kinds such as P3×63Ag8, P3/NS1/1-Ag4-1, and SP-2/0-Ag-14 are known as mouse myeloma cells, and everything are obtained easily.

It is preferable that myeloma cells are HGPRT (hypoxanthine-guanine phosphoribosyltransferase)$^-$ cell lines that can not live in HAT media (a medium containing hypoxanthine, aminopterin, and thymidine), and don't secrete antibodies. SP-2/0-Ag-14 are preferably used.

Then, the obtained cell fusion mixtures are sown in 96 microwell plate at low density, which are cultured in HAT medium. By 1-2 weeks, unfused myeloma cells, hybridomas of myeloma cells, unfused splenic cells, and hybridomas of splenic cells die out, whereas only hybridomas of splenic cells and myeloma cells proliferate.

By reacting culture supernatant of hybridomas with solid phase antigens and measuring the antibodies that specifically adsorbs the antigens by using labeled second antibodies, screening of previous (3) judges whether hybridomas product the antibodies against human membrane protein or human PD-1 or not.

The process of (4) is performed by cloning antibody-producing hybridomas according to soft agar culture (*Monoclonal Antibodies*, 372 (1980)). In this case, it is also possible to use the limiting dilution.

In the process of (5), to obtain a large amount of antibody more efficiently, a method of administrating the hybridomas into mouse peritoneal cavity, and separating and refining them from peritoneal fluid can be used.

In the process of (6), usual methods such as salting out, ion-exchange chromatography, gel filtration, hydrophobic chromatography, and affinity chromatography etc. are used, and more effectively, affinity chromatography using protein A-sepharose CL-4B (Amersham Biosciences K.K.) can be used.

Since the bispecific antibodies of the present invention specifically bind, they can be used for purification and concentration such as affinity chromatography etc. of human PD-1.

In the process of (7), for example, cross linking agents can make sulfo-EMCS(N-(6-maleinimidecaproxy)succinimide sodium salt) bind to SH (mercapto) groups or amide groups of antibodies. First, either of antibodies is referred to amido coupling reactions with sulfo-EMCS. The unreacted sulfo-EMCS is separated by gel filtration. SH (mercapto) groups of the other antibody that have been reduced by 2-mercaptoethylamine etc. are referred to react with maleimide groups of sulfo-EMCS that have bound to the first antibody. The one that two kinds of antibodies were mutually cross-linked is separated by gel filtration.

In the process of (8), each antibody that be obtained in process (6) was digested by pepsin for 48 hours at 37° C. $F(ab')_2$ digested by pepsin are purified by usual methods such as salting out, ion-exchange chromatography, gel filtration, hydrophobic chromatography, and affinity chromatography etc. and more effectively, gel filtration using cefaclor S-200 (Amersham Biosciences K.K.) can be used.

In the process of (9), $F(ab')_2$ are reduced by 2-mercaptoethanol for 30 minutes at 30° C. The reduced $Fab_{SH}$ are purified by usual methods such as salting out, ion-exchange chromatography, gel filtration, hydrophobic chromatography, and affinity chromatography etc. and more effectively, gel filtration using cefaclor S-200 can be used.

In the process of (10), the other antibodies in $Fab_{SH}$ fraction are referred to bind with linkers. Cross linking agents have only to bind mercapto (SH) groups of $Fab_{SH}$, which is referred to react with phenylenedimaleimide for 30 minutes at room temperature. Then, it is referred to react with 1.3 times more the other $Fab_{SH}$ for 4 hours at room temperature. The obtained substance having bivalent specificity are purified by usual methods such as salting out, ion-exchange chromatography, gel filtration, hydrophobic chromatography, and affinity chromatography etc. and more effectively, gel filtration using cefaclor S-200 can be used.

In the process of (11), the antibodies obtained in process (6) can be used as they are, or as the one that are preferably labeled (for example, biotin-labeling and FITC-labeling etc.) by the common procedure. In ELISA, the antibodies are added to solid phase antigens. Then, when using enzyme-labeled secondary antibody and biotin-labeled antibody, the specific binding between the antibodies and the antigens can be measured by absorptiometer under the presence of chromophore substance, after adding enzyme-labeled streptavidin. Low-molecules that specifically recognize PD-1 or the membrane protein can be obtained by using this assay system.

In the process of (12), when the other is an antibody or Fab, it can bind to an antibody or Fab by introducing suitable functional groups to the obtained low-molecules. For example, if maleimide groups are introduced, it can bind to mercapto (SH) groups of the antibody or Fab. If both are low-molecules, molecules including both can be synthesized.

On the other hand, cDNA of each antibody can be separated from hybridomas that produce the monoclonal antibodies against each antigen. By transforming suitable host cells using expression vector containing DNA that both cDNA or partial fragments thereof have been linked by gene recombination methods, the host cells can produce bispecific antibodies.

Concretely, the bispecific antibodies comprising the antibodies against human PD-1 or partial fragments thereof and the antibodies against the membrane protein on cell membrane of human PD-1-expressing cells or partial fragments thereof can be prepared by the following methods;

(1) Each antibody gene is separated from each hybridoma that anti-human PD-1 monoclonal antibodies and anti-membrane protein monoclonal antibodies are respectively produced,
(2) Variable region DNA of anti-human PD-1 monoclonal antibody gene and variable region DNA of anti-membrane protein monoclonal antibody gene are linked by using linker DNA. The expression vectors containing the linked DNA fragments are introduced to suitable host cells,
(3) the cells are cultured under a suitable culture condition, and produced proteins are separated and refined.

Each process is concretely explained as follows.

The process of (1) comprises a process of separating RNA from hybridomas and a process of separating an antibody gene or cDNA encoding partial peptide thereof.

The process of separating the total RNA or mRNA from hybridomas can be performed according to a well-known method (a method described in Sambrook, J., et al, *Molecular Cloning* (1989), Cold Spring Harbor Laboratory, or F. M. Ausubel., et al., *Current Protocol in Molecular Biology*).

By using synthetic DNA primers having partial nucleotide sequences of the antibodies of the present invention, cDNA encoding the antibody genes of the present invention or partial peptide thereof can be amplified by Polymerase Chain Reaction (hereafter, called PCR). Or, by hybridization with probes labeled by using DNA fragments or the synthetic DNAs encoding a part or whole region of the antibodies of the present invention, the cDNA can be selected from cDNA contained in suitable vectors. The hybridization can be performed according to a well-known method. The antibody gene can be amplified by using the total RNA or mRNA by Reverse Transcriptase Polymerase Chain Reaction (Hereafter, called RT-PCR).

(2) As a method of producing the bispecific antibodies of the present invention,
(i) a method of synthesizing peptide and
(ii) a method of producing by gene recombination technologies etc. are enumerated, and the method of the described in (ii) is preferable, industrially.

The expression system (hosts-vector system) to produce peptide by using gene recombination technologies includes, for example, the expression system of *bacillus*, yeasts, insect cells, and mammalian cells.

The vector system includes *E. coli* plasmids (for example, pBR322, pBR325, pUC12, and pUC13), *Bacillus subtilis* plasmids (for example, pUB110, pTP5, and pC194), yeast plasmids (for example, pSH19 and pSH15), bacteriophages such as lambda phage, animal viruses such as retrovirus, vaccinia virus, and baculovirus, PA1-11, pXT1, pRc/CMV, pRc/RSV, and pcDNAI/Neo etc.

The promoter in the present invention has only to be an appropriate promoter corresponding to the gene expression host. For example, when animal cells are used as hosts, SRα promoter, SV40 promoter, LTR promoter, CMV promoter, and HSV-TK promoter etc. are enumerated. It is preferable to use CMV (cytomegalovirus) promoter, SRα promoter etc. In case of *Escherichia coli*, trp promoter, lac promoter, recA promoter, λPL promoter, lpp promoter, and T7 promoter etc. are preferable. In case of *Bacillus* bacterium, SPO1 promoter, SPO2 promoter, and penP promoter etc. are preferable. In case of yeasts, PHO5 promoter, PGK promoter, GAP promoter, and ADH promoter etc. are preferable.

Additionally, the expression vector containing enhancer, splicing signal, polyA signal, selected marker, and SV40 duplication on (hereafter, it may be called SV40ori.) etc. can be used, if necessary. The selected marker includes, for example, dihydrofolate reductase (hereafter, it may be called dhfr.) gene (Methotrexate (MTX) resistance), ampicillin resistance gene (hereafter, it may be called Ampr), and neomycin resistance gene (hereafter, it may be called Neor. G418 resistance) etc. Especially, when dhfr gene is used as a selected marker using dhfr gene deficient chinese hamster cells, a target gene can be selected even by using the medium without thymidine. The signal sequence to suitable for the hosts can be added to N-terminal side of the protein of the present invention, if necessary. When the hosts are *Escherichia*, PhoA signal sequence and OmpA signal sequence etc. can be used. When the hosts are *bacillus*, α-amylase signal sequence and subtilisin signal sequence etc. can be used. When the hosts are *bacillus*, MFα signal sequence, SUC2 signal sequence etc. can be used. When the hosts are animal cells, α-insulin signal sequence, α-interferon signal sequence, and antibody signal sequence etc. can be used, respectively. The transformants can be manufactured using the vector containing DNA encoding the constructed protein of the present invention.

By culturing *Escherichia* transformed with the expression vector in suitable medium, the target peptide is obtained from the body cells. And, if a signal peptide (for example, a signal peptide of pelB) of bacteria is used, the target peptide is secreted in the periplasm. Further, it can be produced as fusion protein with other peptide. In case of the expression in mammalian cells, for example, by culturing mammalian cells transformed by suitable expression vectors including cDNA encoding a target protein in suitable medium, the target peptides are secreted into medium.

For example, *Escherichia*, *Bacillus* bacterium, yeasts, insect cells, insects, and animal cells etc. can be used as host cells. For example, *Escherichia coli* K12, DH1, JM103, JA221, HB101, C600, JM109, DH5, and DH5α etc. can be used as concrete examples of *Escherichia*. For example, *bacillus Bacillus subtilis* M1114 etc. can be used as *Bacillus* bacterium. For example, *Saccharomyces cerevisiae* AH22, AH22R-NA87-11A, DKD-5D, or 20B-12, *Saccharomyces pombe* NCYC1913, or NCYC2036, and *Pichia pastoris* KM71 etc. can be used as yeasts. When virus is AcNPV, for example, *Spodoptera frugiperda* Cell (SF cell), MG1 cells derived from *Trichoplusia ni* midgut, High Five™ cells derived from *Trichoplusia ni* egg, cells derived from *Mamestra brassicae*, cells derived from *Estigmene acrea* etc. can be used as insect cells. When virus is BmNPV, cell lines derived from silkworm (*Bombyx mori* N cells; BmN cells) etc. can be used. For example, Sf9 cells (ATCC CRL1711) (Vaughn, J. L., *In Vivo,* 13; 213-217 (1977)) and Sf21 cells etc. can be used as Sf cells. For example, silkworm larvas etc. can be used as insects. For example, COS-1, COS-7, Vero, chinese hamster cell CHO (hereafter, it's abbreviated with CHO cells.), dhfr-deficient chinese hamster cell CHO (hereafter, it's abbreviated with CHO (dhfr-) cells), mouse L cells, mouse AtT-20, mouse myeloma cells, rat GH3, HEK293 T lymphocytes, and human FL cells etc. can be used as animal cells. For example, *Escherichia* transformation can be performed according to *Proc. Natl. Acad. Sci.* (*USA*), 69, 2110 (1972). For example, *Bacillus* transformation can be performed according to *Molecular & General Genetic,* 168, 111 (1979). For example, yeasts transformation can be performed according to Becker, D M., et al, *Methods in Enzymology,* volume 194, p. 182-187 (1991), or *Proc. Natl. Acad. Sci.* (*USA*), 75, 1929 (1978). Insect cells or insects transformation can be performed according to *Bio/Technology,* 6; 47-55 (1978). Animal cells transformation can be performed according to *CELL TECHNOLOGY SUPPLEMENT* 8 *NEW CELL TECHNOLOGY EXPERIMENTAL PROTOCOL,* Shujunsha, 263 (1995), or *Virology,* 52, 456 (1973).

(3) The obtained peptides are purified by usual methods such as salting out, ion-exchange chromatography, gel filtration, hydrophobic chromatography, and affinity chromatography etc.

In general, a substantially pure polypeptide comprising the amino acid sequence represented by SEQ ID NO:2, SEQ ID NO:4 or SEQ ID NO:11 is a polypeptide containing the amino acid sequence that is 90% or more, 95, 98, or 99% or more homologous to the polypeptide on producing.

A homologue of the substantially pure polypeptide comprising the amino acid sequence represented by SEQ ID NO:2, SEQ ID NO:4 or SEQ ID NO:11 is a polypeptide containing the amino acid sequence that is at least 70% or more, preferably at least 80, 90, or 95% or more homologous to the polypeptide over a region of at least continuous 20 amino acids, preferably at least 30, 40, 60, or 100 amino acids.

A fragment of the substantially pure polypeptide comprising the amino acid sequence represented by SEQ ID NO:2, SEQ ID NO:4 or SEQ ID NO:11 is a polypeptide containing at least 10 amino acids, preferably at least 15, 20, 25, 30, 40, 50, or 60 amino acids, and a homologue thereof is a polypeptide containing the amino acid sequence that is at least 70%, preferably at least 80, 90, or 95% or more homologous to the polypeptide over a region of at least continuous 10 amino acids, preferably at least continuous 15, 20, 25, 30, 40, 50, or 60 amino acids.

A substantially pure polypeptide comprising amino acid sequence that deleted one or several amino acids from a polypeptide comprising the amino acid sequence represented by SEQ ID NO:2, SEQ ID NO:4 or SEQ ID NO:11 is a polypeptide comprising amino acid sequence that deleted one or two amino acids or more (preferably 1 to approx. 25, more preferably 1 to approx. 10, furthermore, preferably 1 to 5) from amino acid sequence.

A substantially pure polypeptide comprising amino acid sequence that has been substituted by one or several amino acids from a polypeptide comprising the amino acid sequence represented by SEQ ID NO:2, SEQ ID NO:4 or SEQ ID NO:11 is a polypeptide comprising amino acid sequence that has been substituted by one or two amino acids or more (preferably 1 to approx. 25, more preferably 1 to approx. 10, furthermore, preferably 1 to 5).

A homologue of a polynucleotide comprising DNA the nucleotide sequence represented by SEQ ID NO:1, SEQ ID NO:3 or SEQ ID NO:9 is a polynucleotide that is at least 70%, preferably at least 80, 90, or more preferably 95% or more homologous to the polynucleotide over a region of at least continuous 20, preferably at least continuous 30, 40, 60, or 100 nucleotide sequence.

A fragment of the polynucleotide comprising DNA the nucleotide sequence represented by SEQ ID NO:1, SEQ ID NO:3 or SEQ ID NO:9 is a polynucleotide containing polynucleotide comprising at least continuous 20, preferably at least continuous 30, 40, 50, 60, or 100 nucleotide sequence.

A DNA hybridizing to DNA containing the nucleotide sequence represented by SEQ ID NO:1, SEQ ID NO:3 or SEQ ID NO:9 under stringent condition includes, for example, approx. a DNA containing nucleotide sequence that is approx. 70% or more, preferably approx. 80% or more, more preferably approx. 90% or more, most preferably approx. 95% or more homologous to nucleotide sequence respectively represented by SEQ ID NO:1, SEQ ID NO:3, or SEQ ID NO:9.

The hybridization can be performed according to a well-known method or, for example, a method described in J. Sambrook, *Molecular Cloning,* 2nd, Coldspring Harbor Laboratory. When using a commercial library, it is possible to perform it according to an attached method described in directions for use. More preferably, it is possible to perform it under stringent condition. High-stringent condition is approx. 19-40 mM, preferably approx. 19-20 mM of NaCl concentration, at approx. 50-70° C., preferably approx. 60-65° C. Approx. 19 mM of sodium concentration at approx. 65° C. is most preferable, especially.

INDUSTRIAL APPLICABILITY

Application to Medicine:

The substance specific to human PD-1 of the present invention can be used for therapy and/or prevention for the following disease.

The substance specific to human PD-1 of the present invention is useful for therapy and/or prevention for neurodegenerative diseases (geriopsychosis, Alzheimer disease, Down syndrome, Parkinson's disease, Creutzfeldt-jakob disease, diabetic neuropathy, Parkinson syndrome, Huntington's disease, Machado-Joseph disease, amyotrophic lateral sclerosis, diabetic neuropathy, and Creutzfeldt Creutzfeldt-Jakob disease).

The substance specific to human PD-1 of the present invention is useful for therapy and/or prevention for diseases that accelerate the immune reaction, for example, autoimmune diseases (glomerular nephritis, arthritis, dilated cardiomyopathy-like disease, ulceous colitis, Sjogren syndrome, Crohn disease, systemic erythematodes, chronic rheumatoid arthritis, multiple sclerosis, psoriasis, allergic contact dermatitis, polymyosiis, pachyderma, periarteritis nodosa, rheumatic fever, vitiligo vulgaris, insulin dependent diabetes mellitus, Behcet disease, Hashimoto disease, Addison disease, dermatomyositis, myasthenia gravis, Reiter syndrome, Graves' disease, anaemia perniciosa, Goodpasture syndrome, sterility disease, chronic active hepatitis, pemphigus, autoimmune thrombopenic purpura, and autoimmune hemolytic anemia).

The substance specific to human PD-1 of the present invention is useful for therapy and/or prevention for collagenosis (systemic lupus erythematous, rheumatoid arthritis, systemic scleroderma, diffuse scleroderma, dermatomyositis, polymyositis, polymyosiis, Sjogren's syndrome, mixed connective tissue disease, polyarteritis nodosa, and rheumatic fever etc.).

The substance specific to human PD-1 of the present invention is useful for therapy and/or prevention for organ graft rejection, allergic disease, and diseases caused by attenuation of immune reaction, which PD-1 participates, for example, tumour and infectious disease.

When using the substance specific to human PD-1 of the present invention for the above purpose, it is usually administered systemically or locally, and orally or parenterally.

The dosage is different depending on age, body weight, symptom, therapeutic effect, administration route, and duration of the treatment etc. For oral administration, generally, the dosage range from 0.1 mg to 100 mg per an adult is orally administered once to several times per day, or the dosage range from 0.01 mg to 30 mg per an adult is administered once to several times per day parenterally, suitably intravenously, and is intravenously administered for 1 to 24 hours per day continuously.

Since the dosage changes depending on various conditions as described above, there are cases in which doses lower or greater than the above dosage may be used.

When a composition of the present invention is administered, it is used as internal solid medicines and internal liquid medicines for internal use, and injections, external preparations, suppositoriums etc. for parenteral administration.

The internal solid medicines for oral administration include compressed tablets, pills, capsules, dispersing powders, granules etc. The capsules include hard capsules and soft capsules.

In case of such the solid medicines, one or more active compound(s) may be pharmaceutically manufactured as itself/themselves or a formulation with excipients (lactose, mannitol, glucose, microcrystal cellulose, and starch etc.), binders (hydroxypropylcellulose, polyvinyl pyrrolidone, and magnesium metasilicate aluminate etc.), disintegrators (cellulose calcium glycolate etc.), lubricants (magnesium stearate etc.), stabilizers, or solubilizers (glutamate and aspartic acid etc.) etc. according to usual methods. Further, they may be optionally coated by coatings (sucrose, gelatin, hydroxypropylcellulose, and hydroxypropylmethylcellulose phthalate etc.) or coated in the layer of two or more. Further, capsules of absorbable materials such as gelatin may be included.

The liquid compositions for oral administration include pharmaceutically acceptable waters, suspensions, emulsions, syrups, and elixirs etc. As to such liquid medicines, one or more active compound(s) may be dissolved, suspended, or emulsified to generally used diluent (purified water, ethanol or those mixing liquids etc.). Further, those liquid medicines may contain humectants, suspending agents, emulsifying agents, sweeteners, flavor agents, flavoring agents, preservatives, and buffers etc.

The injections for parenteral administration include solid injections that are dissolved or suspended to solution, suspension, emulsion, or time of use solvent. The injections are used by dissolving, levigating and melting one or more activator(s) to the solvent. As the solvent, for example, water for injection, distilled saline, vegetable oil, propylene glycol, polyethylene glycol, alcohols such as ethanol etc. and these combinations are used. Further, this injection may include stabilizers, solubilizers (glutamate, aspartic acid, and polysorbate 80 (registered trademark) etc.), suspending agents, emulsifying agents, soothing agents, buffers, and preservatives etc. These are sterilize in the final process or are manufactured from the aseptic manipulation. Aseptic solid medicines may be manufactured as a freeze-drying product and may be used by making to be aseptic or dissolving to aseptic distilled water for injection or other solvents before use.

Other compositions containing one or more activator(s) for parenteral administration include liquid for external use, ointment drug, coating drug, inhalant, aerosol, suppository and pessary for intrarectal administration which is prescribed according to a routine procedure.

The sprays may contain a stabilizer such as sodium hydrogen sulfite besides the diluent generally used, a buffer giving isotonicity, and an isotonic medicine such as, for example, sodium chloride, sodium citrate, or citrates. Production methods of the sprays have been described in, for example, U.S. Pat. No. 2,868,691 specification and U.S. Pat. No. 3,095,355 specification in detail.

Since PD-1 relates to the immune reaction, PD-1 can also be used for screening etc., the substance related to the immune reaction by measuring the expression of human PD-1 using the substance specific to human PD-1 of the present invention.

The substance specific to human PD-1 of the present invention comprises of a part that recognizes human PD-1, a part that recognizes the membrane protein on cell membrane of human PD-1-expressing cells, and a linker, and is an excellent substance that specifically recognizes human PD-1 and the membrane protein, and can transmit human PD-1 signal.

BEST MODE FOR CARRYING OUT THE INVENTION

The following examples explain the present invention more concretely, but don't limit the range of the present invention.

EXAMPLE 1

To obtain DNA encoding anti-human PD-1 antibody and anti-human CD3 antibody respectively, each total RNA was isolated from J110 (International Trust Number: FERM BP-8392) hybridoma and CD3 antibody hybridoma (obtained from ATCC: ATCC Number: CRL-8001). The operation was performed by using SV total Isolation System (trade name: purchase from Promega) according to the manufacturer instructions.

J110 hybridoma cDNA library and CD3 antibody hybridoma cDNA library were generated from total RNA (total RNA) by oligo dT prime method by using Ready-To-Go You-Prime First-Strand Beads (trade name: purchase from Amersham Pharmacia). The operation and procedure were done according to the manufacturer instructions.

cDNA of variable region of each IgG heavy chain and IgG light chain of anti-human PD-1 antibody and anti-human CD3 antibody was amplified by PCR reaction using Heavy Primers and Light Primers (the trade name: purchase from Amersham Pharmacia), respectively. PCR was carried out the following steps; as a first step at 95° C. for 2 minutes and as cycle steps at 95° C. for 30 seconds, at 50° C. for 30 seconds, and at 72° C. for 40 seconds was repeated 30 times and was left at 72° C. for 5 minutes as last step.

PCR product was separated by agarose gel electrophoresis. The expected size of DNA fragment was collected and was cloned into pGEM-T Easy Vector (trade name: purchase from Promega). Then, *E. coli* DH5 (was transformed with the plasmid. DNA of each IgG heavy chain (SEQ ID NO:1 or 5) and IgG light chain (SEQ ID NO:3 or 7) were sequenced to determine the consensus sequence.

EXAMPLE 2

Figure 1:
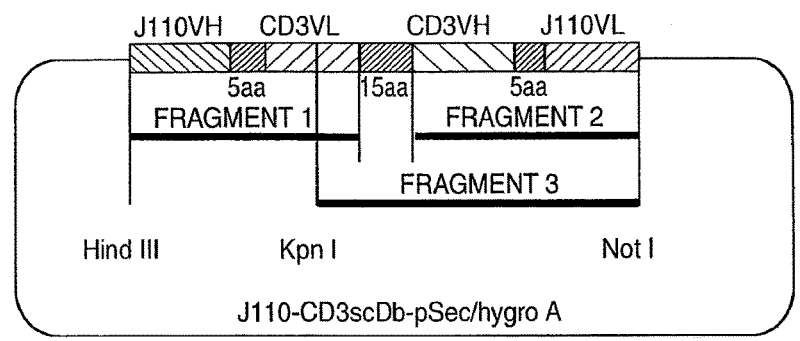
FIG. 1 shows the construction of a bispecific antibody expression vector.
Figure 2:
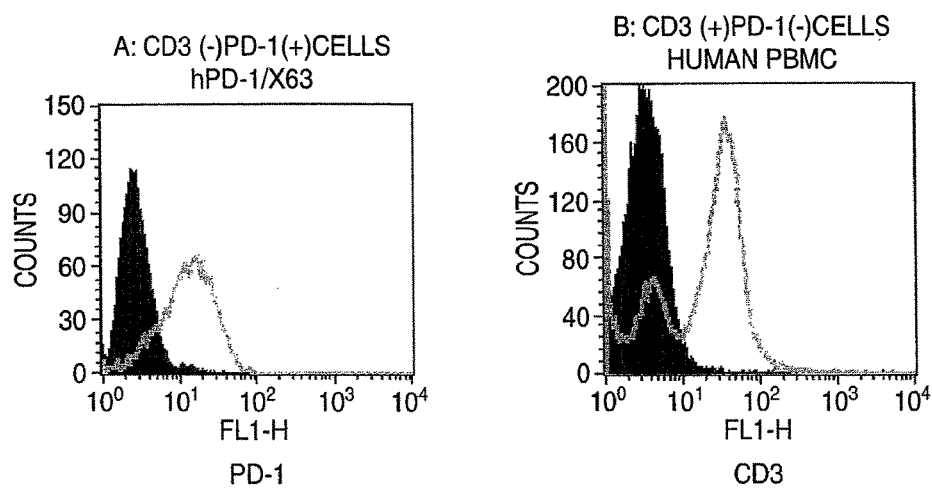
FIG. 2 shows the reactivity of each bispecific antibody against X63 cell surface antigen expressed in CD3(−)/PD-1 (+) cells and peripheral blood mononuclear cells (PBMC) surface antigen as CD3(+)/PD-1 (−) cells. In this figure, filling areas of histogram represent control IgG and opening areas represent distribution of PD-1 or CD3 positive cell.

DNAs encoding bispecific antibodies were prepared by being respectively connected to the separated cDNAs in example 1. Fragment 1 was prepared by connecting IgG heavy chain cDNA (SEQ ID NO:1) of anti-human PD-1 antibody and IgG light chain cDNA (SEQ ID NO:7) of anti-human CD3 antibody by PCR using linker No. 1 (SEQ ID NO:19), linker No. 2 (SEQ ID NO:20), primer No. 1 (SEQ ID NO:14), and primer No. 2 (SEQ ID NO:15) (FIG. 1). Fragment 2 was prepared by connecting IgG heavy chain cDNA (SEQ ID NO:7) of anti-human CD3 antibody and IgG light chain cDNA (SEQ ID NO:1) of anti-human PD-1 antibody by PCR using linker No. 3 (SEQ ID NO:21), linker No. 4 (SEQ ID NO:22), primer No. 3 (SEQ ID NO:16), and primer No. 4 (SEQ ID NO:17) (FIG. 1). Fragment 3 was prepared (FIG. 1) by connecting fragment 1 and fragment 2 by PCR using linker No. 5 (SEQ ID NO:23), linker No. 6 (SEQ ID NO:24), primer No. 5 (SEQ ID NO:18), and primer No. 4 (SEQ ID NO:22) and then the nucleotide sequence was decided (SEQ ID NO:9).

Each PCR reaction was respectively performed. First PCR was performed by repeating 20 times the following steps; at 94(C for 30 seconds, at 40(C for 30 seconds, and at 72(C for 50 seconds. 2nd PCR was performed by repeating 30 times the following steps; at 94(C for 30 seconds, at 50(C for 30 seconds, and at 72(C for 50 seconds, by using first PCR solution as a template.

Primer No. 2:
(SEQ ID NO: 14)
5'-TTTTTTAAGCTTACAGGTCCAGCTGCAGGAGTCA-3'

Primer No. 2:
(SEQ ID NO: 15)
5'-TTTTTTGCGGCCGCCCGGTTTATTTCCAACTTTG-3'

Primer No. 3:
(SEQ ID NO: 16)
5'-TTTTTTAAGCTTACAGGTCCAGCTGCAGCAGTCT-3'

Primer No. 4:
(SEQ ID NO: 17)
5'-TTTTTTGCGGCCGCCCGTTTGATTTCCAGCTTGG-3'

Primer No. 5:
(SEQ ID NO: 18)
5'-ATGAACTGGTACCAGCAGAAG-3'

Linker No. 1:
(SEQ ID NO: 19)
5'-AGGGACCACGGTCACCGTCTCCTCAGGTGGAGGCGGTTCACAAATTG
TTCTCACCCAGTCTCCAG-3'

Linker No. 2:
(SEQ ID NO: 20)
5'-CTGGAGACTGGGTGAGAACAATTTGTGAACCGCCTCCACCTGAGGAG
ACGGTGACCGTGGTCCCT-3'

Linker No. 3:
(SEQ ID NO: 21)
5'-AGGCACCACTCTCACAGTCTCCTCAGGTGGAGGCGGTTCAGACATCC
AGATGACCCAGTCTCCAG-3'

Linker No. 4:
(SEQ ID NO: 22)
5'-CTGGAGACTGGGTCATCTGGATGTCTGAACCGCCTCCACCTGAGGAG
ACTGTGAGAGTGGTGCCT-3'

Linker No. 5:
(SEQ ID NO: 23)
5'-GGGGACAAAGTTGGAAATAAACCGGGGTGGAGGCGGTTCAGGCGGAG
GTGGCTCTGGCGGTGGCGGATCGCAGGTCCAGCTGCAGCAGTCTGGGG-3'

Linker No. 6:
(SEQ ID NO: 24)
5'-CCCCAGACTGCTGCAGCTGGACCTGCGATCCGCCACCGCCAGAGCCA
CCTCCGCCTGAACCGCCTCCACCCCGGTTTATTTCCAACTTTGTCCCC-3'

DNA encoding the bispecific antibody prepared by the above method was cloned into expression vector pSecTag2/HygroA (trade name: purchase from Invitrogen). First, each of fragment 1 and fragment 3 was digested by restriction enzyme HindIII, KpnI, KpnI, and NotI and then was purified by agarose electrophoresis. Then, the DNA fragments were ligated in a HindIII and NotI digested pSecTag2/HygroA vector. *E. coli* DH5 (was transformed with the plasmid J110-CD3scDb-pSec/hygroA encoding the bispecific antibody was amplified, extracted, and purified (FIG. 1).

EXAMPLE 3

Bispecific antibody protein was prepared by J110-CD3scDb-pSec/hygroA expression plasmid. The construct was transiently transfected into human kidney cell line 293T (ATCC Number: CRL-11268) with LipofectAMINE-plus (trade name: purchased from Invitrogen) and cultured for four days. The supernatant was sterilized with 0.22 μm PVDF filter, and was concentrated using 40% PEG20000 solution. The concentrated supernatant was purified by HiTrap Chelating HP column (trade name: purchased from Amershampharmacia).

EXAMPLE 4

The reactivity of the bispecific antibody (PD-1 and CD3) binding to cell surface antigens analyzed by FACScan.

1 or 10 μg of the bispecific antibodies were respectively added to human PD-1-expressed X63 cell lines as PD-1 positive/CD3 negative cells (CD3(−)/PD-1 (+) cells) and human peripheral blood mononuclear cells as PD-1 negative/CD3 positive cells (CD3(+)/PD-1 (−) cells), and incubated on ice. Immediately second antibodies were added and incubate on ice for 30 min. It was confirmed that the bispecific antibodies reacted to PD-1 and CD3.

EXAMPLE 5

The activity of the bispecific antibody was evaluated as an effect on the proliferation of activated human peripheral blood T cells.

Concretely, PBMC were isolated from peripheral blood samples of healthy donors by Lymphoprep Tube (trade name: purchased from HYCOMED PHARMA). The operation and procedure were done according to the manufacturer instructions. Erythricytes were removed from PBMC by lysis with lysis buffer (0.8% $NH_4Cl$, 0.1% $KCO_3$, 1 mM EDTA). And purified T cell passed through Nylon Fiber ColumnT (trade name: purchased from Rosh) were resuspended to medium (RPMI1640 medium including 10% fetal bovine serum).

Figure 3:
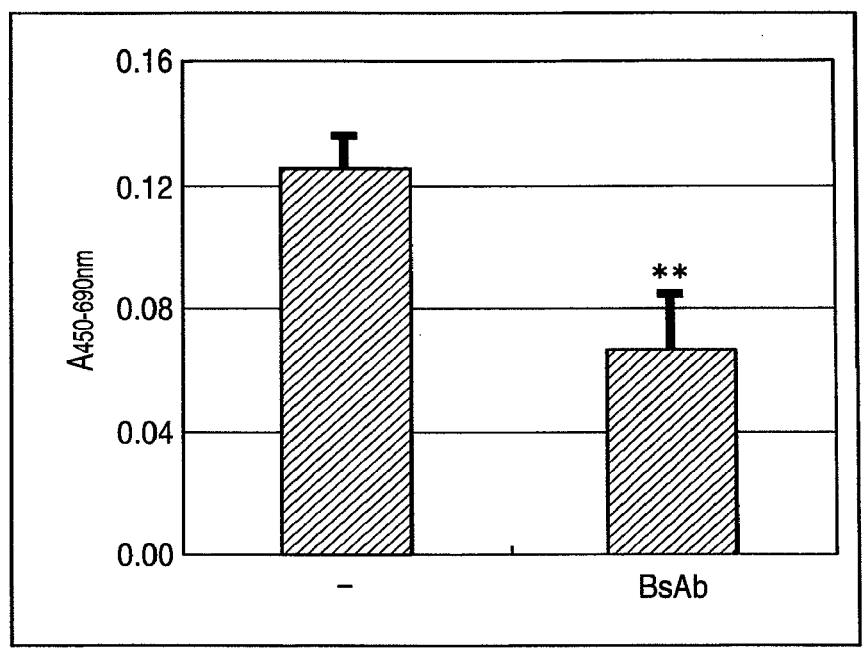
FIG. 3 shows the effect on proliferative response of activated human peripheral blood T cells of bispecific antibody. In this figure, "-" represents Control IgG-adding group and "BsAb" represents the bispecific antibody-adding group, the spindle represents measurement absorbance, and ** represents $P<0.05$ in significance test.

Purified T cell ($2\times10^6$/mL/well) were cultured for 60 hours with 1 μg/ml anti-human CD28 antibody (the clone name: CD28.2 and purchased from Pharmingen) in 24 well-plate that has were pre-coated with 5 μg/ml anti-human αβTCR antibody (the clone name: T10B9.1A-31 and purchased from Pharmingen). Activated T cells were rested for 12 hours, and resting T cells ($1\times10^6$/100 μl/well) were restimulated adding 1 μg/well of bispecific antibody in 96 well-plate that were pre-coated with 0.1 μg/ml anti-αβTCR antibody. 48 hours later, T cell proliferation was determined—by BrdU incorporation using Cell Proliferation ELISA (the trade name: purchased from Rosh). FIG. 3 shows the result.

The bispecific antibodies have significantly decreased the proliferation of the activated human peripheral blood T cells.

---

The invention claimed is:

1. A method for inhibiting the proliferation of activated T cells, comprising administering an effective amount of a bispecific antibody to a patient in need thereof, wherein the bispecific antibody comprises the following parts;
   (a) VH region of anti-human PD-1 antibody;
   (b) VL region of anti-human CD3 antibody;
   (c) VH region of said anti-human CD3 antibody; and
   (d) VL region of said anti-human PD-1 antibody,
   and simultaneously binds to both of human PD-1 and human CD3.

2. The method according to claim 1, wherein human CD3 is human CD3 epsilon.

3. The method according to claim 1, wherein the bispecific antibody is a complete monoclonal antibody.

4. The method according to claim 1, wherein
   (a) the VH region of anti-human PD-1 antibody comprises amino acids having the sequence set forth in SEQ ID NO: 2,
   (b) the VL region of anti-human CD3 antibody comprises amino acids having the sequence set forth in SEQ ID NO: 8,
   (c) the VH region of said anti-human CD3 antibody comprises amino acids having the sequence set forth in SEQ ID NO: 6 and
   (d) the VL region of said anti-human PD-1 antibody comprises amino acids having the sequence set forth in SEQ ID NO: 4.

5. The method according to claim 1, wherein the disease treated by inhibiting the proliferation of activated T-cells is autoimmune disease or collagenosis.

6. The method according to claim 5, wherein the autoimmune disease is a disease selected from the group consisting of ulcerative colitis, Sjogren's syndrome, Crohn's disease, systemic lupus erythematodes, chronic rheumatoid arthritis, multiple sclerosis, psoriasis, polymyositis, periarteritis nodosa, rheumatic fever, insulin dependent diabetes mellitus, Behcet's disease, Hashimoto's disease, Addison's disease, dermatomyositis, Myasthenia gravis, Reiter's syndrome, Graves' disease, Goodpasture's syndrome, pemphigus, autoimmune thrombocytopenic purpura, and autoimmune hemolytic anemia.

7. The method according to claim 5, wherein the autoimmune disease is selected from the group consisting of insulin dependent diabetes mellitus, ulcerative colitis, Crohn's disease, systemic lupus erythematodes and multiple sclerosis.

8. The method according to claim 5, wherein the collagenosis is selected from the group consisting of systemic lupus erythematous, rheumatoid arthritis, systemic scleroderma, diffuse scleroderma, dermatomyositis, polymyositis, Sjogren's syndrome, mixed connective tissue disease, polyarteritis nodosa, and rheumatic fever.

* * * * *

SEQUENCE LISTING

<160> NUMBER OF SEQ ID NOS: 26

<210> SEQ ID NO 1
<211> LENGTH: 357
<212> TYPE: DNA
<213> ORGANISM: Mus musculus

<400> SEQUENCE: 1

```
caggtccagc tgcaggagtc aggacctggc ctggtgaaac cttctcagtc tctgtccctc      60
acctgcactg tcactggcca ctcaatcacc agtgattatg cctggaactg gatccggcag     120
tttccaggag acaaactgga gtggatgggc tacataagct acagtggtta cactacctac     180
aacccatctc tgaaaagtcg agtctctatc actcgagaca catccaagaa ccagttcttc     240
ctgcagttga attctgtgac tactgaggac acagccacat acttctgtgc aagagacctt     300
gattacggcc cctggtttgc ttactggggc caagggacca cggtcaccgt ctcctca      357
```

<210> SEQ ID NO 2
<211> LENGTH: 119
<212> TYPE: PRT
<213> ORGANISM: Mus musculus

<400> SEQUENCE: 2

```
Gln Val Gln Leu Gln Glu Ser Gly Pro Gly Leu Val Lys Pro Ser Gln
1               5                   10                  15

Ser Leu Ser Leu Thr Cys Thr Val Thr Gly His Ser Ile Thr Ser Asp
            20                  25                  30

Tyr Ala Trp Asn Trp Ile Arg Gln Phe Pro Gly Asp Lys Leu Glu Trp
        35                  40                  45

Met Gly Tyr Ile Ser Tyr Ser Gly Tyr Thr Thr Tyr Asn Pro Ser Leu
    50                  55                  60

Lys Ser Arg Val Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Phe Cys
                85                  90                  95

Ala Arg Asp Leu Asp Tyr Gly Pro Trp Phe Ala Tyr Trp Gly Gln Gly
            100                 105                 110

Thr Thr Val Thr Val Ser Ser
        115
```

<210> SEQ ID NO 3

```
<211> LENGTH: 324
<212> TYPE: DNA
<213> ORGANISM: Mus musculus

<400> SEQUENCE: 3
gacatccaga tgacccagtc tccagcctcc ctatctgcat ctgtgggaga aactgtcacc    60
ctcacatgtc gagcaagtga gaatattcac aattatttag catggtatca gcagaaacag   120
ggaaaatctc ctcagctcct ggtctataat gtaaaaacct tagcagatgg tgtgccatca   180
aggttcagtg gcagtggatc aggaacacaa tattctctca agatcaacag cctgcagcct   240
gaagattttg ggagttatta ctgtcaacat ttttggagta gtccgtggac gttcggtgga   300
ggcaccaagc tggaaatcaa acgg                                          324

<210> SEQ ID NO 4
<211> LENGTH: 108
<212> TYPE: PRT
<213> ORGANISM: Mus musculus

<400> SEQUENCE: 4

Asp Ile Gln Met Thr Gln Ser Pro Ala Ser Leu Ser Ala Ser Val Gly
1               5                   10                  15

Glu Thr Val Thr Leu Thr Cys Arg Ala Ser Glu Asn Ile His Asn Tyr
            20                  25                  30

Leu Ala Trp Tyr Gln Lys Gln Gly Lys Ser Pro Gln Leu Leu Val
        35                  40                  45

Tyr Asn Val Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ser Pro Trp
                85                  90                  95

Thr Phe Gly Gly Gly Thr Lys Leu Glu Ile Lys Arg
            100                 105

<210> SEQ ID NO 5
<211> LENGTH: 357
<212> TYPE: DNA
<213> ORGANISM: Mus musculus

<400> SEQUENCE: 5
caggtccagc tgcagcagtc tggggctgaa ctggcaagac ctggggcctc agtgaagatg    60
tcctgcaagg cttctggcta cacctttact aggtacacga tgcactgggt aaaacagagg   120
cctggacagg gtctggaatg gattggatac attaatccta gccgtggtta ctaattac    180 aatcagaagt tcaaggacaa ggccacattg actacagaca atcctccag cacagcctac   240 atgcaactga gcagcctgac atctgaggac tctgcagtct attactgtgc aagatattat   300
gatgatcatt actgccttga ctactggggc caaggcacca ctctcacagt ctcctca     357

<210> SEQ ID NO 6
<211> LENGTH: 119
<212> TYPE: PRT
<213> ORGANISM: Mus musculus

<400> SEQUENCE: 6

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
```

```
            20                  25                  30
Thr Met His Trp Val Lys Gln Arg Pro Gly Gln Gly Leu Glu Trp Ile
         35                  40                  45

Gly Tyr Ile Asn Pro Ser Arg Gly Tyr Thr Asn Tyr Asn Gln Lys Phe
     50                  55                  60

Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
                100                 105                 110

Thr Thr Leu Thr Val Ser Ser
             115
```

<210> SEQ ID NO 7
<211> LENGTH: 321
<212> TYPE: DNA
<213> ORGANISM: Mus musculus

<400> SEQUENCE: 7

```
caaattgttc tcacccagtc tccagcaatc atgtctgcat ctccagggga gaaggtcacc     60
atgacctgca gtgccagctc aagtgtaagt tacatgaact ggtaccagca gaagtcaggc    120
acctccccca aagatggat ttatgacaca tccaaactgg cttctggagt ccctgctcac     180
ttcaggggca gtgggtctgg gacctcttac tctctcacaa tcagcggcat ggaggctgaa    240
gatgctgcca cttattactg ccagcagtgg agtagtaacc cattcacgtt cggctcgggg    300
acaaagttgg aaataaaccg g                                              321
```

<210> SEQ ID NO 8
<211> LENGTH: 107
<212> TYPE: PRT
<213> ORGANISM: Mus musculus

<400> SEQUENCE: 8

```
Gln Ile Val Leu Thr Gln Ser Pro Ala Ile Met Ser Ala Ser Pro Gly
  1               5                  10                  15

Glu Lys Val Thr Met Thr Cys Ser Ala Ser Ser Ser Val Ser Tyr Met
             20                  25                  30

Asn Trp Tyr Gln Gln Lys Ser Gly Thr Ser Pro Lys Arg Trp Ile Tyr
         35                  40                  45

Asp Thr Ser Lys Leu Ala Ser Gly Val Pro Ala His Phe Arg Gly Ser
     50                  55                  60

Gly Ser Gly Thr Ser Tyr Ser Leu Thr Ile Ser Gly Met Glu Ala Glu
 65                  70                  75                  80

Asp Ala Ala Thr Tyr Tyr Cys Gln Gln Trp Ser Ser Asn Pro Phe Thr
                 85                  90                  95

Phe Gly Ser Gly Thr Lys Leu Glu Ile Asn Arg
                100                 105
```

<210> SEQ ID NO 9
<211> LENGTH: 1982
<212> TYPE: DNA
<213> ORGANISM: Artificial Sequence
<220> FEATURE:
<223> OTHER INFORMATION: Chemically-synthesized polynucleotide sequence
      encoding bispecific antibody

<400> SEQUENCE: 9

```
aatgggagtt tgttttggca ccaaaatcaa cgggactttc caaaatgtcg taacaactcc      60
gccccattga cgcaaatggg cggtaggcgt gtacggtggg aggtctatat aagcagagct     120
ctctggctaa ctagagaacc cactgcttac tggcttatcg aaattaatac gactcactat     180
agggagaccc aagctggcta gccaccatgg agacagacac actcctgcta tgggtactgc     240
tgctctgggt tccaggttcc actggtgacg cggcccagcc ggccaggcgc gccgtacgaa     300
gcttacaggt ccagctgcag gagtcaggac ctggcctggt gaaaccttct cagtctctgt     360
ccctcacctg cactgtcact ggccactcaa tcaccagtga ttatgcctgg aactggatcc     420
ggcagtttcc aggagacaaa ctggagtgga tgggctacat aagctacagt ggttacacta     480
cctacaaccc atctctgaaa agtcgagtct ctatcactcg agacacatcc aagaaccagt     540
tcttcctgca gttgaattct gtgactactg aggacacagc cacatacttc tgtgcaagag     600
accttgatta cggcccctgg tttgcttact ggggccaagg gaccacggtc accgtctcct     660
caggtggagg cggttcacaa attgttctca cccagtctcc agcaatcatg tctgcatctc     720
caggggagaa ggtcaccatg acctgcagtg ccagctcaag tgtaagttac atgaactggt     780
accagcagaa gtcaggcacc tcccccaaaa gatggattta tgacacatcc aaactggctt     840
ctggagtccc tgctcacttc aggggcagtg gtctgggac ctcttactct ctcacaatca     900
gcggcatgga ggctgaagat gctgccactt attactgcca gcagtggagt agtaacccat     960
tcacgttcgg ctcggggaca aagttggaaa taaaccgggg tggaggcggt tcaggcggag    1020
gtggctctgg cggtggcgga tcgcaggtcc agctgcagca gtctggggct gaactggcaa    1080
gacctggggc ctcagtgaag atgtcctgca aggcttctgg ctacacctt actaggtaca    1140
cgatgcactg ggtaaaacag aggcctggac agggtctgga atggattgga tacattaatc    1200
ctagccgtgg ttatactaat tacaatcaga agttcaagga caaggccaca ttgactacag    1260
acaaatcctc cagcacagcc tacatgcaac tgagcagcct gacatctgag gactctgcag    1320
tctattactg tgcaagatat tatgatgatc attactgcct tgactactgg ggccaaggca    1380
ccactctcac agtctcctca ggtggaggcg gttcagacat ccagatgacc cagtctccag    1440
cctccctatc tgcatctgtg ggagaaactg tcaccctcac atgtcgagca gtgagaata    1500
ttcacaatta tttagcatgg tatcagcaga acagggaaa atctcctcag ctcctggtct    1560
ataatgtaaa aaccttagca gatggtgtgc catcaaggtt cagtggcagt ggatcaggaa    1620
cacaatattc tctcaagatc aacagcctgc agcctgaaga ttttgggagt tattactgtc    1680
aacattttg gagtagtccg tggacgttcg gtggaggcac caagctggaa atcaaacggg    1740
cggccgctcg aggagggccc gaacaaaaac tcatctcaga agaggatctg aatagcgccg    1800
tcgaccatca tcatcatcat cattgagttt aaacccgctg atcagcctcg actgtgcctt    1860
ctagttgcca gccatctgtt gtttgcccct ccccgtgcc ttccttgacc ctggaaggtg    1920
ccactcccac tgtcctttcc taataaaatg aggaaattgc atcgcattgt ctgagtaggt    1980
gt                                                                  1982
```

<210> SEQ ID NO 10
<211> LENGTH: 1982
<212> TYPE: DNA
<213> ORGANISM: Artificial Sequence
<220> FEATURE:
<223> OTHER INFORMATION: Chemically-synthesized polynucleotide and
      polypeptide sequence encoding bispecific antibody
<220> FEATURE:
<221> NAME/KEY: CDS

<222> LOCATION: (207)..(1823)

<400> SEQUENCE: 10

```
aatgggagtt tgttttggca ccaaaatcaa cgggactttc caaaatgtcg taacaactcc      60
gccccattga cgcaaatggg cggtaggcgt gtacggtggg aggtctatat aagcagagct     120
ctctggctaa ctagagaacc cactgcttac tggcttatcg aaattaatac gactcactat     180
agggagaccc aagctggcta gccacc atg gag aca gac aca ctc ctg cta tgg      233
                              Met Glu Thr Asp Thr Leu Leu Leu Trp
                               1               5 gta ctg ctg ctc tgg gtt cca ggt tcc act ggt gac gcg gcc cag ccg       281
Val Leu Leu Leu Trp Val Pro Gly Ser Thr Gly Asp Ala Ala Gln Pro
 10              15                  20                  25 gcc agg cgc gcc gta cga agc tta cag gtc cag ctg cag gag tca gga       329
Ala Arg Arg Ala Val Arg Ser Leu Gln Val Gln Leu Gln Glu Ser Gly
             30                  35                  40 cct ggc ctg gtg aaa cct tct cag tct ctg tcc ctc acc tgc act gtc       377
Pro Gly Leu Val Lys Pro Ser Gln Ser Leu Ser Leu Thr Cys Thr Val
         45                  50                  55 act ggc cac tca atc acc agt gat tat gcc tgg aac tgg atc cgg cag       425
Thr Gly His Ser Ile Thr Ser Asp Tyr Ala Trp Asn Trp Ile Arg Gln
     60                  65                  70 ttt cca gga gac aaa ctg gag tgg atg ggc tac ata agc tac agt ggt       473
Phe Pro Gly Asp Lys Leu Glu Trp Met Gly Tyr Ile Ser Tyr Ser Gly
 75                  80                  85 tac act acc tac aac cca tct ctg aaa agt cga gtc tct atc act cga       521
Tyr Thr Thr Tyr Asn Pro Ser Leu Lys Ser Arg Val Ser Ile Thr Arg
 90                  95                 100                 105 gac aca tcc aag aac cag ttc ttc ctg cag ttg aat tct gtg act act       569
Asp Thr Ser Lys Asn Gln Phe Phe Leu Gln Leu Asn Ser Val Thr Thr
                110                 115                 120 gag gac aca gcc aca tac ttc tgt gca aga gac ctt gat tac ggc ccc       617
Glu Asp Thr Ala Thr Tyr Phe Cys Ala Arg Asp Leu Asp Tyr Gly Pro
            125                 130                 135 tgg ttt gct tac tgg ggc caa ggg acc acg gtc acc gtc tcc tca ggt       665
Trp Phe Ala Tyr Trp Gly Gln Gly Thr Thr Val Thr Val Ser Ser Gly
        140                 145                 150 gga ggc ggt tca caa att gtt ctc acc cag tct cca gca atc atg tct       713
Gly Gly Gly Ser Gln Ile Val Leu Thr Gln Ser Pro Ala Ile Met Ser
    155                 160                 165 gca tct cca ggg gag aag gtc acc atg acc tgc agt gcc agc tca agt       761
Ala Ser Pro Gly Glu Lys Val Thr Met Thr Cys Ser Ala Ser Ser Ser
170                 175                 180                 185 gta agt tac atg aac tgg tac cag cag aag tca ggc acc tcc ccc aaa       809
Val Ser Tyr Met Asn Trp Tyr Gln Gln Lys Ser Gly Thr Ser Pro Lys
                190                 195                 200 aga tgg att tat gac aca tcc aaa ctg gct tct gga gtc cct gct cac       857
Arg Trp Ile Tyr Asp Thr Ser Lys Leu Ala Ser Gly Val Pro Ala His
            205                 210                 215 ttc agg ggc agt ggg tct ggg acc tct tac tct ctc aca atc agc ggc       905
Phe Arg Gly Ser Gly Ser Gly Thr Ser Tyr Ser Leu Thr Ile Ser Gly
        220                 225                 230 atg gag gct gaa gat gct gcc act tat tac tgc cag cag tgg agt agt       953
Met Glu Ala Glu Asp Ala Ala Thr Tyr Tyr Cys Gln Gln Trp Ser Ser
    235                 240                 245 aac cca ttc acg ttc ggc tcg ggg aca aag ttg gaa ata aac cgg ggt      1001
Asn Pro Phe Thr Phe Gly Ser Gly Thr Lys Leu Glu Ile Asn Arg Gly
250                 255                 260                 265 gga ggc ggt tca ggc gga ggt ggc tct ggc ggt ggc gga tcg cag gtc      1049
```

```
Gly Gly Gly Ser Gly Gly Gly Ser Gly Gly Gly Ser Gln Val
            270             275             280 cag ctg cag cag tct ggg gct gaa ctg gca aga cct ggg gcc tca gtg      1097
Gln Leu Gln Gln Ser Gly Ala Glu Leu Ala Arg Pro Gly Ala Ser Val
            285                 290                 295 aag atg tcc tgc aag gct tct ggc tac acc ttt act agg tac acg atg      1145
Lys Met Ser Cys Lys Ala Ser Gly Tyr Thr Phe Thr Arg Tyr Thr Met
            300                 305                 310 cac tgg gta aaa cag agg cct gga cag ggt ctg gaa tgg att gga tac      1193
His Trp Val Lys Gln Arg Pro Gly Gln Gly Leu Glu Trp Ile Gly Tyr
            315                 320                 325 att aat cct agc cgt ggt tat act aat tac aat cag aag ttc aag gac      1241
Ile Asn Pro Ser Arg Gly Tyr Thr Asn Tyr Asn Gln Lys Phe Lys Asp
330                 335                 340                 345 aag gcc aca ttg act aca gac aaa tcc tcc agc aca gcc tac atg caa      1289
Lys Ala Thr Leu Thr Thr Asp Lys Ser Ser Ser Thr Ala Tyr Met Gln
                350                 355                 360 ctg agc agc ctg aca tct gag gac tct gca gtc tat tac tgt gca aga      1337
Leu Ser Ser Leu Thr Ser Glu Asp Ser Ala Val Tyr Tyr Cys Ala Arg
                365                 370                 375 tat tat gat gat cat tac tgc ctt gac tac tgg ggc caa ggc acc act      1385
Tyr Tyr Asp Asp His Tyr Cys Leu Asp Tyr Trp Gly Gln Gly Thr Thr
            380                 385                 390 ctc aca gtc tcc tca ggt gga ggc ggt tca gac atc cag atg acc cag      1433
Leu Thr Val Ser Ser Gly Gly Gly Gly Ser Asp Ile Gln Met Thr Gln
395                 400                 405 tct cca gcc tcc cta tct gca tct gtg gga gaa act gtc acc ctc aca      1481
Ser Pro Ala Ser Leu Ser Ala Ser Val Gly Glu Thr Val Thr Leu Thr
410                 415                 420                 425 tgt cga gca agt gag aat att cac aat tat tta gca tgg tat cag cag      1529
Cys Arg Ala Ser Glu Asn Ile His Asn Tyr Leu Ala Trp Tyr Gln Gln
                430                 435                 440 aaa cag gga aaa tct cct cag ctc ctg gtc tat aat gta aaa acc tta      1577
Lys Gln Gly Lys Ser Pro Gln Leu Leu Val Tyr Asn Val Lys Thr Leu
            445                 450                 455 gca gat ggt gtg cca tca agg ttc agt ggc agt gga tca gga aca caa      1625
Ala Asp Gly Val Pro Ser Arg Phe Ser Gly Ser Gly Ser Gly Thr Gln
                460                 465                 470 tat tct ctc aag atc aac agc ctg cag cct gaa gat ttt ggg agt tat      1673
Tyr Ser Leu Lys Ile Asn Ser Leu Gln Pro Glu Asp Phe Gly Ser Tyr
475                 480                 485 tac tgt caa cat ttt tgg agt agt ccg tgg acg ttc ggt gga ggc acc      1721
Tyr Cys Gln His Phe Trp Ser Ser Pro Trp Thr Phe Gly Gly Gly Thr
490                 495                 500                 505 aag ctg gaa atc aaa cgg gcg gcc gct cga gga ggg ccc gaa caa aaa      1769
Lys Leu Glu Ile Lys Arg Ala Ala Ala Arg Gly Gly Pro Glu Gln Lys
                510                 515                 520 ctc atc tca gaa gag gat ctg aat agc gcc gtc gac cat cat cat cat      1817
Leu Ile Ser Glu Glu Asp Leu Asn Ser Ala Val Asp His His His His
            525                 530                 535 cat cat tgagtttaaa cccgctgatc agcctcgact gtgccttcta gttgccagcc       1873
His His atctgttgtt tgcccctccc ccgtgccttc cttgaccctg gaaggtgcca ctcccactgt    1933
cctttcctaa taaaatgagg aaattgcatc gcattgtctg agtaggtgt                1982

<210> SEQ ID NO 11
<211> LENGTH: 539
<212> TYPE: PRT
<213> ORGANISM: Artificial Sequence
```

<220> FEATURE:
<223> OTHER INFORMATION: Chemically-synthesized polypeptide sequence
      encoding bispecific antibody

<400> SEQUENCE: 11

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Val Arg Ser
            20                  25                  30

Leu Gln Val Gln Leu Gln Glu Ser Gly Pro Gly Leu Val Lys Pro Ser
        35                  40                  45

Gln Ser Leu Ser Leu Thr Cys Thr Val Thr Gly His Ser Ile Thr Ser
    50                  55                  60

Asp Tyr Ala Trp Asn Trp Ile Arg Gln Phe Pro Gly Asp Lys Leu Glu
65                  70                  75                  80

Trp Met Gly Tyr Ile Ser Tyr Ser Gly Tyr Thr Thr Tyr Asn Pro Ser
                85                  90                  95

Leu Lys Ser Arg Val Ser Ile Thr Arg Asp Thr Ser Lys Asn Gln Phe
            100                 105                 110

Phe Leu Gln Leu Asn Ser Val Thr Thr Glu Asp Thr Ala Thr Tyr Phe
        115                 120                 125

Cys Ala Arg Asp Leu Asp Tyr Gly Pro Trp Phe Ala Tyr Trp Gly Gln
    130                 135                 140

Gly Thr Thr Val Thr Val Ser Ser Gly Gly Gly Ser Gln Ile Val
145                 150                 155                 160

Leu Thr Gln Ser Pro Ala Ile Met Ser Ala Ser Pro Gly Glu Lys Val
                165                 170                 175

Thr Met Thr Cys Ser Ala Ser Ser Val Ser Tyr Met Asn Trp Tyr
            180                 185                 190

Gln Gln Lys Ser Gly Thr Ser Pro Lys Arg Trp Ile Tyr Asp Thr Ser
        195                 200                 205

Lys Leu Ala Ser Gly Val Pro Ala His Phe Arg Gly Ser Gly Ser Gly
    210                 215                 220

Thr Ser Tyr Ser Leu Thr Ile Ser Gly Met Glu Ala Glu Asp Ala Ala
225                 230                 235                 240

Thr Tyr Tyr Cys Gln Gln Trp Ser Ser Asn Pro Phe Thr Phe Gly Ser
                245                 250                 255

Gly Thr Lys Leu Glu Ile Asn Arg Gly Gly Gly Ser Gly Gly Gly
            260                 265                 270

Gly Ser Gly Gly Gly Ser Gln Val Gln Leu Gln Gln Ser Gly Ala
        275                 280                 285

Glu Leu Ala Arg Pro Gly Ala Ser Val Lys Met Ser Cys Lys Ala Ser
    290                 295                 300

Gly Tyr Thr Phe Thr Arg Tyr Thr Met His Trp Val Lys Gln Arg Pro
305                 310                 315                 320

Gly Gln Gly Leu Glu Trp Ile Gly Tyr Ile Asn Pro Ser Arg Gly Tyr
                325                 330                 335

Thr Asn Tyr Asn Gln Lys Phe Lys Asp Lys Ala Thr Leu Thr Thr Asp
            340                 345                 350

Lys Ser Ser Ser Thr Ala Tyr Met Gln Leu Ser Ser Leu Thr Ser Glu
        355                 360                 365

Asp Ser Ala Val Tyr Tyr Cys Ala Arg Tyr Tyr Asp Asp His Tyr Cys
    370                 375                 380

Leu Asp Tyr Trp Gly Gln Gly Thr Thr Leu Thr Val Ser Ser Gly Gly
```

```
            385                 390                 395                 400
Gly Gly Ser Asp Ile Gln Met Thr Gln Ser Pro Ala Ser Leu Ser Ala
                405                 410                 415

Ser Val Gly Glu Thr Val Thr Leu Thr Cys Arg Ala Ser Glu Asn Ile
                420                 425                 430

His Asn Tyr Leu Ala Trp Tyr Gln Gln Lys Gln Gly Lys Ser Pro Gln
                435                 440                 445

Leu Leu Val Tyr Asn Val Lys Thr Leu Ala Asp Gly Val Pro Ser Arg
            450                 455                 460

Phe Ser Gly Ser Gly Ser Gly Thr Gln Tyr Ser Leu Lys Ile Asn Ser
465                 470                 475                 480

Leu Gln Pro Glu Asp Phe Gly Ser Tyr Tyr Cys Gln His Phe Trp Ser
                485                 490                 495

Ser Pro Trp Thr Phe Gly Gly Gly Thr Lys Leu Glu Ile Lys Arg Ala
                500                 505                 510

Ala Ala Arg Gly Gly Pro Glu Gln Lys Leu Ile Ser Glu Glu Asp Leu
                515                 520                 525

Asn Ser Ala Val Asp His His His His His His
            530                 535
```

<210> SEQ ID NO 12
<211> LENGTH: 1617
<212> TYPE: DNA
<213> ORGANISM: Artificial Sequence
<220> FEATURE:
<223> OTHER INFORMATION: Chemically-synthesized polynucleotide sequence
      encoding bispecific antibody <400> SEQUENCE: 12

```
atggagacag acacactcct gctatgggta ctgctgctct ggttccagg ttccactggt      60 gacgcggccc agccggccag gcgcgccgta cgaagcttac aggtccagct gcaggagtca    120
ggacctggcc tggtgaaacc ttctcagtct ctgtccctca cctgcactgt cactggccac    180
tcaatcacca gtgattatgc ctggaactgg atccggcagt ttccaggaga caaactggag    240
tggatgggct acataagcta cagtggttac actacctaca acccatctct gaaaagtcga    300
gtctctatca ctcgagacac atccaagaac cagttcttcc tgcagttgaa ttctgtgact    360
actgaggaca cagccacata cttctgtgca agagaccttg attacggccc tggtttgct    420 tactggggcc aagggaccac ggtcaccgtc tcctcaggtg aggcggttc acaaattgtt    480 ctcacccagt ctccagcaat catgtctgca tctccagggg agaaggtcac catgacctgc    540
agtgccagct caagtgtaag ttacatgaac tggtaccagc agaagtcagg cacctccccc    600
aaaagatgga tttatgacac atccaaactg gcttctggag tccctgctca cttcaggggc    660
agtgggtctg ggacctctta ctctctcaca atcagcggca tggaggctga agatgctgcc    720
acttattact gccagcagtg gagtagtaac ccattcacgt tcggctcggg gacaaagttg    780
gaaataaacc ggggtggagg cggttcaggc ggaggtggct ctggcggtgg cggatcgcag    840
gtccagctgc agcagtctgg ggctgaactg gcaagacctg ggcctcagt gaagatgtcc    900 tgcaaggctt ctggctacac ctttactagg tacacgatgc actgggtaaa acagaggcct    960
ggacagggtc tggaatggat tggatacatt aatcctagcc gtggttatac taattacaat   1020
cagaagttca aggacaaggc cacattgact acagacaaat cctccagcac agcctacatg   1080
caactgagca gcctgacatc tgaggactct gcagtctatt actgtgcaag atattatgat   1140
gatcattact gccttgacta ctggggccaa ggcaccactc tcacagtctc ctcaggtgga   1200
```

```
ggcggttcag acatccagat gacccagtct ccagcctccc tatctgcatc tgtgggagaa    1260
actgtcaccc tcacatgtcg agcaagtgag aatattcaca attatttagc atggtatcag    1320
cagaaacagg gaaatctcc tcagctcctg gtctataatg taaaaacctt agcagatggt     1380
gtgccatcaa ggttcagtgg cagtggatca ggaacacaat attctctcaa gatcaacagc    1440
ctgcagcctg aagattttgg gagttattac tgtcaacatt tttggagtag tccgtggacg    1500
ttcggtggag gcaccaagct ggaaatcaaa cgggcggccg ctcgaggagg gcccgaacaa    1560
aaactcatct cagaagagga tctgaatagc gccgtcgacc atcatcatca tcatcat       1617
```

<210> SEQ ID NO 13
<211> LENGTH: 1434
<212> TYPE: DNA
<213> ORGANISM: Artificial Sequence
<220> FEATURE:
<223> OTHER INFORMATION: Chemically-synthesized polynucleotide sequence encoding bispecific antibody

<400> SEQUENCE: 13

```
caggtccagc tgcaggagtc aggacctggc ctggtgaaac cttctcagtc tctgtccctc     60
acctgcactg tcactggcca ctcaatcacc agtgattatg cctggaactg gatccggcag    120
tttccaggag acaaactgga gtggatgggc tacataagct acagtggtta cactacctac    180
aacccatctc tgaaaagtcg agtctctatc actcgagaca catccaagaa ccagttcttc    240
ctgcagttga attctgtgac tactgaggac acagccacat acttctgtgc aagagaccct    300
gattacggcc cctggtttgc ttactggggc caagggacca cggtcaccgt ctcctcaggt    360
ggaggcggtt cacaaattgt tctcacccag tctccagcaa tcatgtctgc atctccaggg    420
gagaaggtca ccatgacctg cagtgccagc tcaagtgtaa gttacatgaa ctggtaccag    480
cagaagtcag gcacctcccc caaaagatgg atttatgaca catccaaact ggcttctgga    540
gtccctgctc acttcagggg cagtgggtct gggacctctt actctctcac aatcagcggc    600
atggaggctg aagatgctgc cacttattac tgccagcagt ggagtagtaa cccattcacg    660
ttcggctcgg gacaaagtt ggaaataaac cggggtggag cggttcagg cggaggtggc      720 tctggcggtg cggatcgca ggtccagctg cagcagtctg gggctgaact ggcaagacct     780
ggggcctcag tgaagatgtc ctgcaaggct tctggctaca cctttactag gtacacgatg    840
cactgggtaa acagaggcc tggacagggt ctggaatgga ttggatacat taatcctagc    900
cgtggttata ctaattacaa tcagaagttc aaggacaagg ccacattgac tacagacaaa    960
tcctccagca cagcctacat gcaactgagc agcctgacat ctgaggactc tgcagtctat   1020
tactgtgcaa gatattatga tgatcattac tgccttgact actggggcca aggcaccact   1080
ctcacagtct cctcaggtgg aggcggttca gacatccaga tgacccagtc tccagcctcc   1140
ctatctgcat ctgtgggaga aactgtcacc tcacatgtc gagcaagtga gaatattcac    1200
aattatttag catggtatca gcagaaacag ggaaatctc ctcagctcct ggtctataat    1260
gtaaaaacct tagcagatgg tgtgccatca aggttcagtg gcagtggatc aggaacacaa   1320
tattctctca agatcaacag cctgcagcct gaagattttg ggagttatta ctgtcaacat   1380
ttttggagta gtccgtggac gttcggtgga ggcaccaagc tggaaatcaa acgg         1434
```

<210> SEQ ID NO 14
<211> LENGTH: 34
<212> TYPE: DNA
<213> ORGANISM: Artificial Sequence

```
<220> FEATURE:
<223> OTHER INFORMATION: Chemically-synthesized PCR primer
      oligonucleotide

<400> SEQUENCE: 14 tttttttaagc ttacaggtcc agctgcagga gtca                              34

<210> SEQ ID NO 15
<211> LENGTH: 34
<212> TYPE: DNA
<213> ORGANISM: Artificial Sequence
<220> FEATURE:
<223> OTHER INFORMATION: Chemically-synthesized PCR primer
      oligonucleotide

<400> SEQUENCE: 15 tttttttgcgg ccgcccggtt tatttccaac tttg                              34

<210> SEQ ID NO 16
<211> LENGTH: 34
<212> TYPE: DNA
<213> ORGANISM: Artificial Sequence
<220> FEATURE:
<223> OTHER INFORMATION: Chemically-synthesized PCR primer
      oligonucleotide

<400> SEQUENCE: 16 tttttttaagc ttacaggtcc agctgcagca gtct                              34

<210> SEQ ID NO 17
<211> LENGTH: 34
<212> TYPE: DNA
<213> ORGANISM: Artificial Sequence
<220> FEATURE:
<223> OTHER INFORMATION: Chemically-synthesized PCR primer
      oligonucleotide

<400> SEQUENCE: 17 tttttttgcgg ccgcccgttt gatttccagc ttgg                              34

<210> SEQ ID NO 18
<211> LENGTH: 21
<212> TYPE: DNA
<213> ORGANISM: Artificial Sequence
<220> FEATURE:
<223> OTHER INFORMATION: Chemically-synthesized PCR primer
      oligonucleotide

<400> SEQUENCE: 18
atgaactggt accagcagaa g                                             21

<210> SEQ ID NO 19
<211> LENGTH: 65
<212> TYPE: DNA
<213> ORGANISM: Artificial Sequence
<220> FEATURE:
<223> OTHER INFORMATION: Chemically-synthesized Linker oligonucleotide

<400> SEQUENCE: 19
agggaccacg gtcaccgtct cctcaggtgg aggcggttca caaattgttc tcacccagtc   60
tccag                                                               65

<210> SEQ ID NO 20
<211> LENGTH: 65
<212> TYPE: DNA
<213> ORGANISM: Artificial Sequence
```

```
<220> FEATURE:
<223> OTHER INFORMATION: Chemically-synthesized Linker oligonucleotide

<400> SEQUENCE: 20
ctggagactg ggtgagaaca atttgtgaac cgcctccacc tgaggagacg gtgaccgtgg    60
tccct                                                                65

<210> SEQ ID NO 21
<211> LENGTH: 65
<212> TYPE: DNA
<213> ORGANISM: Artificial Sequence
<220> FEATURE:
<223> OTHER INFORMATION: Chemically-synthesized Linker oligonucleotide

<400> SEQUENCE: 21
aggcaccact ctcacagtct cctcaggtgg aggcggttca gacatccaga tgacccagtc    60
tccag                                                                65

<210> SEQ ID NO 22
<211> LENGTH: 65
<212> TYPE: DNA
<213> ORGANISM: Artificial Sequence
<220> FEATURE:
<223> OTHER INFORMATION: Chemically-synthesized Linker oligonucleotide

<400> SEQUENCE: 22
ctggagactg ggtcatctgg atgtctgaac cgcctccacc tgaggagact gtgagagtgg    60
tgcct                                                                65

<210> SEQ ID NO 23
<211> LENGTH: 95
<212> TYPE: DNA
<213> ORGANISM: Artificial Sequence
<220> FEATURE:
<223> OTHER INFORMATION: Chemically-synthesized Linker oligonucleotide

<400> SEQUENCE: 23
ggggacaaag ttggaaataa accggggtgg aggcggttca ggcggaggtg gctctggcgg    60
tggcggatcg caggtccagc tgcagcagtc tgggg                               95

<210> SEQ ID NO 24
<211> LENGTH: 95
<212> TYPE: DNA
<213> ORGANISM: Artificial Sequence
<220> FEATURE:
<223> OTHER INFORMATION: Chemically-synthesized Linker oligonucleotide

<400> SEQUENCE: 24
ccccagactg ctgcagctgg acctgcgatc cgccaccgcc agagccacct ccgcctgaac    60
cgcctccacc ccggtttatt tccaactttg tcccc                               95

<210> SEQ ID NO 25
<211> LENGTH: 5
<212> TYPE: PRT
<213> ORGANISM: Artificial Sequence
<220> FEATURE:
<223> OTHER INFORMATION: Chemically-synthesized Linker polypeptide

<400> SEQUENCE: 25

Gly Gly Gly Gly Ser
1               5
```

```
<210> SEQ ID NO 26
<211> LENGTH: 15
<212> TYPE: PRT
<213> ORGANISM: Artificial Sequence
<220> FEATURE:
<223> OTHER INFORMATION: Chemically-synthesized Linker polypeptide

<400> SEQUENCE: 26

Gly Gly Gly Gly Ser Gly Gly Gly Gly Ser Gly Gly Gly Gly Ser
1               5                   10                  15
```